US009066703B2

(12) United States Patent
Miller

(10) Patent No.: US 9,066,703 B2
(45) Date of Patent: Jun. 30, 2015

(54) MEDICAL ULTRASOUND 2-D TRANSDUCER ARRAY ARCHITECTURE: SPOT OF ARAGO

(75) Inventor: Gregg Miller, Boulder, CO (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 118 days.

(21) Appl. No.: 12/794,486

(22) Filed: Jun. 4, 2010

(65) Prior Publication Data

US 2011/0301467 A1 Dec. 8, 2011

(51) Int. Cl.
*A61B 8/14* (2006.01)
*A61B 8/00* (2006.01)
*G01S 7/52* (2006.01)
*G01S 15/89* (2006.01)

(52) U.S. Cl.
CPC ............. *A61B 8/4477* (2013.01); *A61B 8/4483* (2013.01); *A61B 8/54* (2013.01); *G01S 7/52047* (2013.01); *G01S 15/8913* (2013.01); *G01S 15/8927* (2013.01)

(58) Field of Classification Search
USPC ................... 600/437–472; 310/320, 321, 332
See application file for complete search history.

(56) References Cited

U.S. PATENT DOCUMENTS

| 4,265,126 | A | * | 5/1981 | Papadofrangakis et al. ........................ 73/861.25 |
|---|---|---|---|---|
| 4,523,471 | A | * | 6/1985 | Lee ................................. 73/626 |
| 5,398,216 | A | * | 3/1995 | Hall et al. ........................ 367/90 |
| 5,485,843 | A | * | 1/1996 | Greenstein et al. ........... 600/455 |
| 5,522,393 | A | * | 6/1996 | Phillips et al. ................. 600/455 |
| 5,893,832 | A | * | 4/1999 | Song .............................. 600/443 |
| 5,911,692 | A | * | 6/1999 | Hussain et al. ............... 600/447 |
| 6,135,963 | A | * | 10/2000 | Haider .......................... 600/447 |
| 6,602,194 | B2 | * | 8/2003 | Roundhill et al. ............ 600/443 |
| 6,783,497 | B2 | | 8/2004 | Grenon et al. |
| 7,559,897 | B2 | * | 7/2009 | Cerofolini ..................... 600/459 |
| 2003/0220554 | A1 | * | 11/2003 | Grenon et al. ................ 600/407 |

FOREIGN PATENT DOCUMENTS

| JP | 6-181929 | 7/1994 |
|---|---|---|
| JP | 7-59773 | 3/1995 |

(Continued)

OTHER PUBLICATIONS

Office Action issued Feb. 17, 2015 in Japanese Patent Application No. 2011-106478.

*Primary Examiner* — Long V. Le
*Assistant Examiner* — Lawrence Laryea
(74) *Attorney, Agent, or Firm* — Oblon, McClelland, Maier & Neustadt, L.L.P.

(57) ABSTRACT

An ultrasound device including a main processing unit, a probe part, an array, and an apodization unit that receives an ultrasound signal from the array, the signal having multiple channels, that determines a weight for each channel based on an apodization profile being one of ring-centered and edge-centered, and that multiplies the received ultrasound signal by the determined weight for each channel. The array includes a first area including a first plurality of elements having a first functionality, a second area including a second plurality of elements having a second functionality, and a third area including a third plurality of elements having a third functionality different from the first functionality. The second area further includes a fourth area having a number of elements that are switchable between the second and third types of functionality. The array also includes a dynamic spot including the third and fourth areas.

33 Claims, 36 Drawing Sheets

(56) References Cited

FOREIGN PATENT DOCUMENTS

| | | |
|---|---|---|
| JP | 8-500023 | 1/1996 |
| JP | 9-313487 | 12/1997 |
| JP | 2005-40376 | 2/2005 |
| JP | 2006-122657 | 5/2006 |
| JP | 2009-153945 | 7/2009 |

* cited by examiner

US 9,066,703 B2

MEDICAL ULTRASOUND 2-D TRANSDUCER ARRAY ARCHITECTURE: SPOT OF ARAGO

BACKGROUND OF THE INVENTION

1. Field of the Invention

The present invention relates to a system and method of producing ultrasound images using a reduced number of transducers elements.

2. Discussion of the Background

Conventionally, two dimensional 2-D ultrasound transducer arrays are formed by simultaneously transmitting and receiving using a plurality of individual transducer elements which act in concert as an array. When using a large number of individual transducer elements, the material cost and power required can be significant. U.S. Pat. No. 6,783,497 (herein Document 1) describes a sparse array that using only a portion of the full populated array. The sparse array consists of two or more separate zones for transmitting and receiving. However, since Document 1 is static in size and has a circular aperture shape, the device described in Document 1 is not sufficiently responsive.

SUMMARY OF THE INVENTION

Accordingly, an embodiment of the present invention provides, inter alia, an ultrasound device including a main processing unit, a probe part connected to the main processing unit, an apodization unit that receives an ultrasound signal from the array, the signal having multiple channels, that determines a weight for each channel based on an apodization profile, the apodization profile being one of ring-centered and/or edge-centered, and that multiplies the received ultrasound signal by the determined weight for each channel, and an array integral to the handle part of the probe. The array includes a first area including a first plurality of elements of a first type having a first functionality, a second area including a second plurality of elements of a second type having a second functionality, and a third area including a third plurality of elements of a third type having a third functionality different from the first functionality. The second area includes further area including a number of elements that are switchable between the second and third types of functionality.

An embodiment of the present invention also provides an ultrasound transducer having an array of elements arranged in an elliptical shape. The array includes a first area including a first plurality of elements of a first type having a first functionality, a second area including a second plurality of elements of a second type having a second functionality and a third area including a third plurality of elements of a third type having a third functionality.

Moreover, an embodiment of the present invention also provides for a method of processing an ultrasound signal obtained using an array including a first area including a first plurality of elements of a first type having a first functionality, a second area including a second plurality of elements of a second type having a second functionality, and a third area including a third plurality of elements of a third type having a third functionality different from the first functionality, wherein the second area further includes a fourth area having a number of elements that are switchable between the second and third types of functionality. The method includes the steps of receiving an ultrasound signal from the array, the signal having multiple channels, determining a weight for each channel based on an apodization profile, multiplying the received ultrasound signal by the determined weight for each channel and displaying the multiplied ultrasound signal as an ultrasound image. In addition, the apodization profile is one of ring-centered and/or inner-edge centered.

It is to be understood that both the foregoing general description of the invention and the following detailed description are exemplary, but are not restrictive, of the invention.

BRIEF DESCRIPTION OF THE DRAWINGS

In the drawings like reference numbers designate identical or corresponding parts throughout the several views. Other objects, features and advantages of an embodiment of the present invention will become more apparent from the following detailed description when read in conjunction with the accompanying drawings, in which.

DETAILED DESCRIPTION OF THE INVENTIONS

Figure 1A:
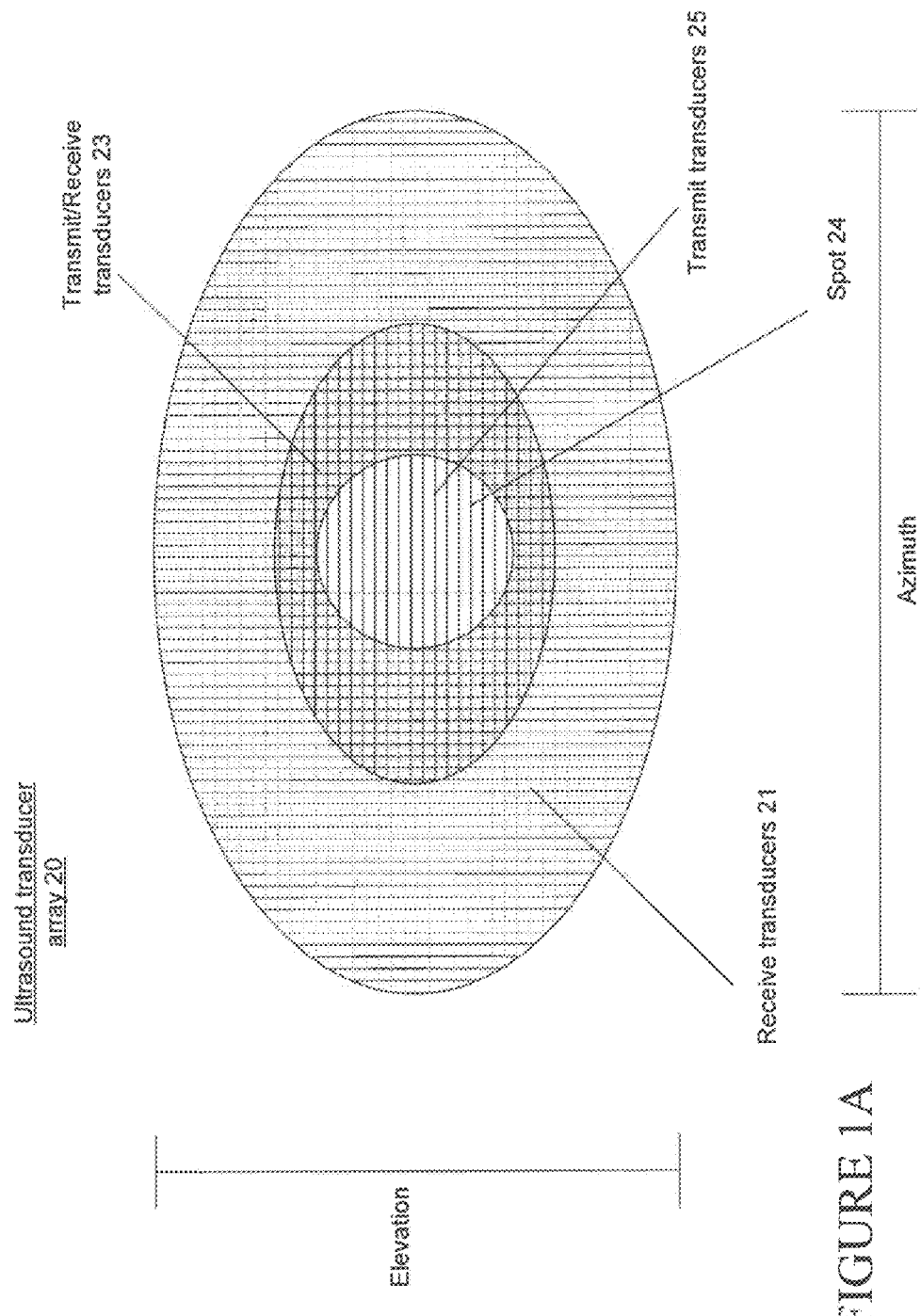
FIG. 1A illustrates an ultrasound transducer array according to an embodiment of the present invention having an elliptical aperture and a circular spot and having a receive only area, a transmit/receive area and a transmit only spot area.

In an embodiment of the present invention there is described a transducer array such as an ultrasound transducer array. Embodiments of the present invention include transducer arrays of a two dimensional (2-D) type. These arrays can include piezoelectric transducers, CMUTS, PMUTSs, or any other suitable type of transducer.

The architecture according to an embodiment of the present invention includes a spot on the transducer array which is not active during transmit and/or receive.

One advantage of this architecture is that the architecture results in a very narrow receive beam width are thereby enhancing near-field lateral resolution and the related imaging quality performance improvements. Moreover, the reduction in the number of elements coupled with similar superior resolution performance reduces power and electronics hardware requirements and saves related material cost.

As a result of the non-active elements in the array having no active transducers, the array has the potential to produce a higher quality near field image. This effect is produced as a result of Fresnel diffraction effects. [Note: Fresnel diffraction refers to near field effects, and Fraunhofer diffraction refers to far field effects.]

This improved signal quality in the near field is analogous to the "spot of Arago" or "Poisson's spot" effect found in optics. The spot of Arago is a term used in optics diffraction theory to describe the result when an opaque circular disk having a size corresponding to a first Fresnel zone is substituted for the aperture of the first Fresnel zone. In such a situation, one would expect that the light amplitude would be reduced by a factor of 2 (for the 2 Fresnel ring case), but instead the irradiance at the center of the shadow is the same and more finely focused as compared with no opaque disk present.

In the case of the present architecture, the non-functioning elements in the spot area, correlate with the opaque optical disk which produces the spot of Arago, provide a focused beam in the near-field which improves image quality. Use of dedicated element clusters at the center of the array, which can be, for example, unused elements, lowers the required number of receive and/or transmit elements which, in turn, lowers the power and cost requirements for the electronics.

The spot noted above may be many different shapes. For instance, in the case of two dimensional (2D) externally utilized cardiac probes, the aperture is generally shaped as a rectangle. The overall probe shape is rectangular, but the spot will still be circular or elliptical in shape. Moreover, optics theory suggests that focusing provided by the Spot of Arago effect is typically realized with circular apertures. However, it has been discovered that an elliptically-shaped "hole" at the center of the aperture does not dramatically alter the beam characteristics when compared with a circular-shaped "hole." Furthermore, elliptically shaped "spots" at the array center will look more circular when the beam is steered (from a point in line with the focus direction), and will therefore create a more focused near-field beam pattern than a circular "spot" under these circumstances.

The elliptical shaped spot is particularly helpful when steering due to the fact that, in the steering process, the ellipse collapses by the cosine of the interrogation angle to come closer to a circular aperture as seen from the line of steering, thereby compensating for this "stretching" of the non-transmitting/non-receiving aperture. Some compensative shaping of the spot can take place when steering (within a beam for receive, and from beam to beam as the line of sight changes, for both transmit and receive), such that it is more circular at receive (or transmit) angles closer to 0 degrees, and more elliptical at receive (or transmit) angles greater than or less than 0 degrees.

Shown below in Table I is a number of different embodiments of the present invention. The list of structures in Table I is not exhaustive.

| | 1 | 2 | 3 |
|---|---|---|---|
| 1 | RECEIVE ONLY | TRANSMIT/RECEIVE | TRANSMIT |
| 2 | RECEIVE ONLY | TRANSMIT/RECEIVE | RECEIVE |
| 3 | RECEIVE ONLY | TRANSMIT/RECEIVE | SPOT (DISABLED) |
| 4 | RECEIVE ONLY | TRANSMIT/RECEIVE | SPOT (DISABLED), RX AND TX DIFFERENT SPOT SIZE |
| 5 | RECEIVE ONLY | TRANSMIT/RECEIVE | SPOT (DISABLED), RX AND TX DIFFERENT SPOT SIZE, RX SPOT DYNAMIC DURING A BEAM |
| 6 | RECEIVE ONLY | TRANSMIT/RECEIVE | SPOT (DISABLED), RX AND TX DIFFERENT SPOT SIZE, RX SPOT DYNAMIC, DURING A BEAM TX AND RX SPOT SIZE CHANGE (OR NOT) FROM BEAM TO BEAM |
| 7 | | TRANSMIT/RECEIVE | TRANSMIT |
| 8 | | TRANSMIT/RECEIVE | RECEIVE |
| 9 | | TRANSMIT/RECEIVE | SPOT (DISABLED) |
| 10 | | TRANSMIT/RECEIVE | SPOT (DISABLED), RX AND TX DIFFERENT SPOT SIZE |
| 11 | | TRANSMIT/RECEIVE | SPOT (DISABLED), RX AND TX DIFFERENT SPOT SIZE, RX SPOT DYNAMIC |
| 12 | | TRANSMIT/RECEIVE | SPOT (DISABLED), RX AND TX DIFFERENT SPOT SIZE, RX SPOT DYNAMIC, DURING A BEAM TX AND RX SPOT SIZE CHANGE (OR NOT) FROM BEAM TO BEAM |
| 13 | TRANSMIT ONLY | TRANSMIT/RECEIVE | TRANSMIT |
| 14 | TRANSMIT ONLY | TRANSMIT/RECEIVE | RECEIVE |
| 15 | TRANSMIT ONLY | TRANSMIT/RECEIVE | SPOT (DISABLED) |
| 16 | TRANSMIT ONLY | TRANSMIT/RECEIVE | SPOT (DISABLED), RX AND TX DIFFERENT SPOT SIZE |
| 17 | TRANSMIT ONLY | TRANSMIT/RECEIVE | SPOT (DISABLED), RX AND TX DIFFERENT SPOT SIZE, RX SPOT DYNAMIC |
| 18 | TRANSMIT ONLY | TRANSMIT/RECEIVE | SPOT (DISABLED), RX AND TX DIFFERENT SPOT SIZE, RX SPOT DYNAMIC, DURING A BEAM TX AND RX SPOT SIZE CHANGE (OR NOT) FROM BEAM TO BEAM |

Embodiment 1

Circular Spot

FIG. 1A illustrates an ultrasound transducer array 20 having a circular spot 24 and that includes receive-only elements 21, transmit/receive elements 23 and transmit-only elements 25 in the spot area 24. The receive-only elements 21 are transducers that exclusively receive reflected ultrasound reverberations. The transmit-only elements 25 in the spot 24 exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 2A:
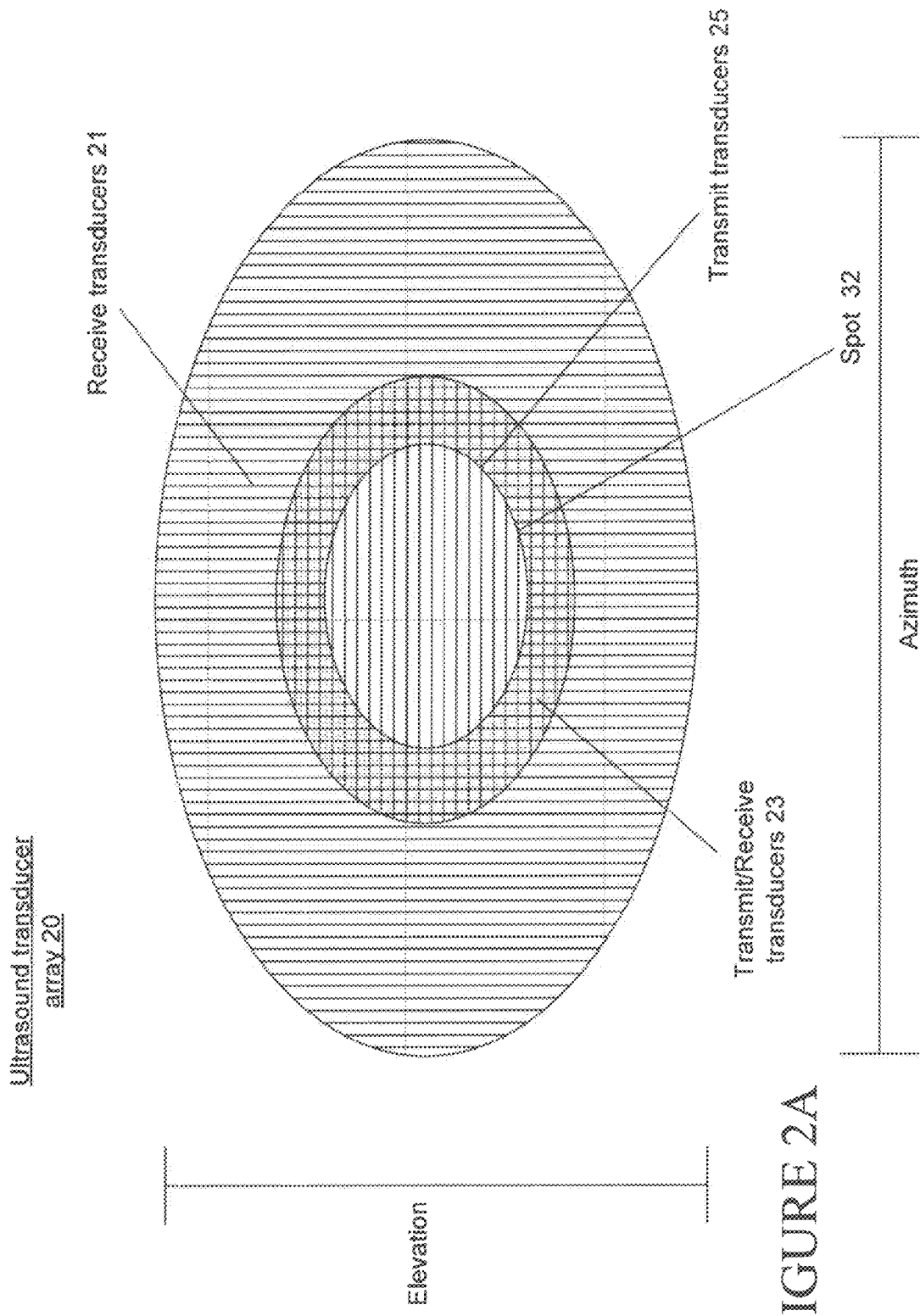
FIG. 2A illustrates an ultrasound transducer array according to an embodiment of the present invention having an elliptical aperture and an elliptical spot and having a receive only area, a transmit/receive area and a transmit only spot area.

FIG. 2A illustrates an ultrasound transducer array 20 having an elliptical spot 32 and that includes receive-only elements 21, transmit/receive elements 23 and transmit-only elements 25 in the spot area 32. The receive-only elements 21 are transducers that exclusively receive reflected ultrasound reverberations. The transmit-only elements 25 in the spot 32 exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

Embodiment 2

Circular Spot

Figure 1B:
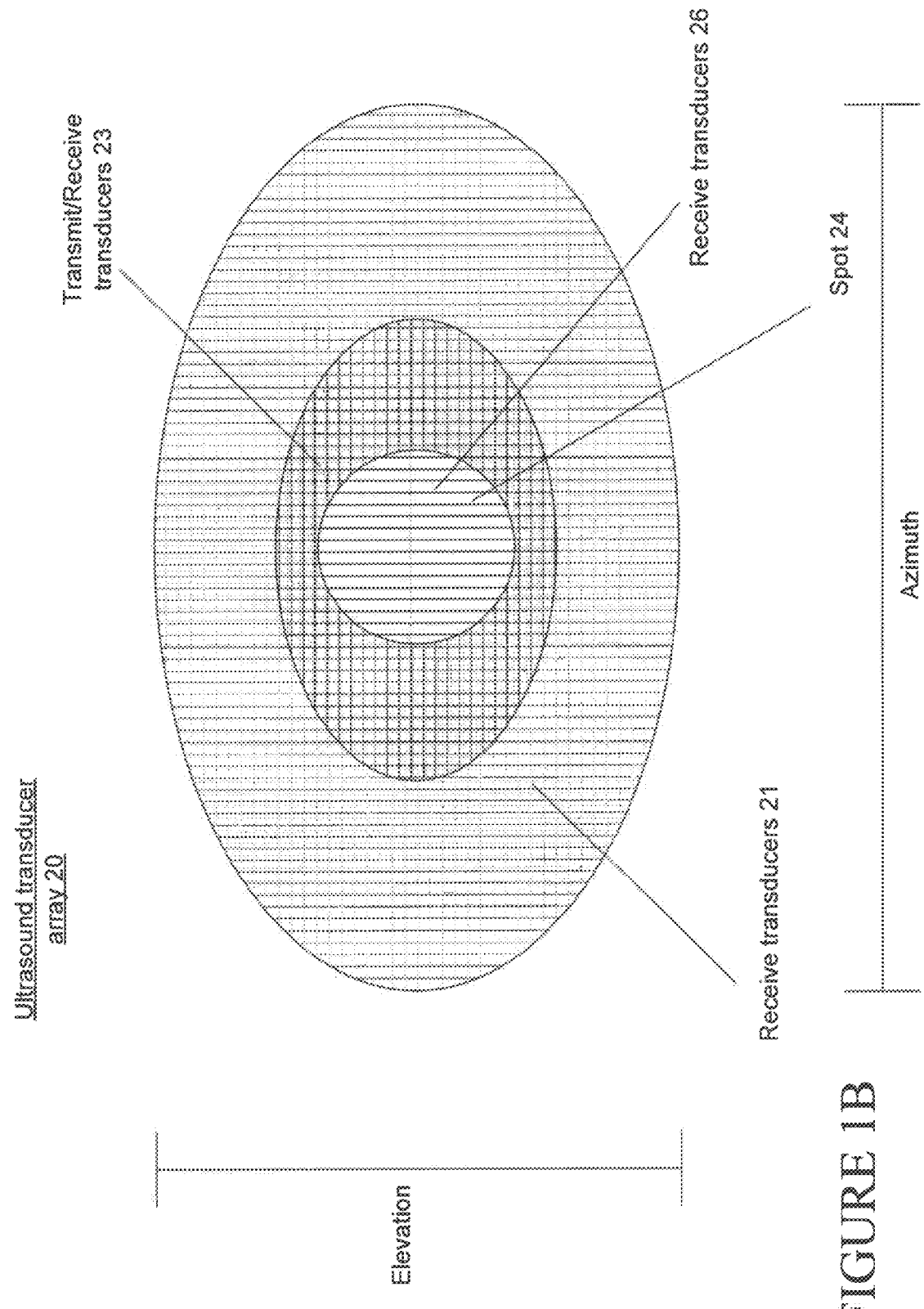
FIG. 1B illustrates an ultrasound transducer array according to an embodiment of the present invention having an elliptical aperture and a circular spot and having a receive only area, a transmit/receive area and a receive only spot area.

FIG. 1B illustrates an ultrasound transducer array 20 having a circular spot 24 and that includes receive-only elements 21, transmit/receive elements 23 and receive-only elements 26 in the spot area 24. The receive-only elements 21 are transducers that exclusively receive reflected ultrasound reverberations. The receive-only elements 26 in the spot 24 also exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 2B:
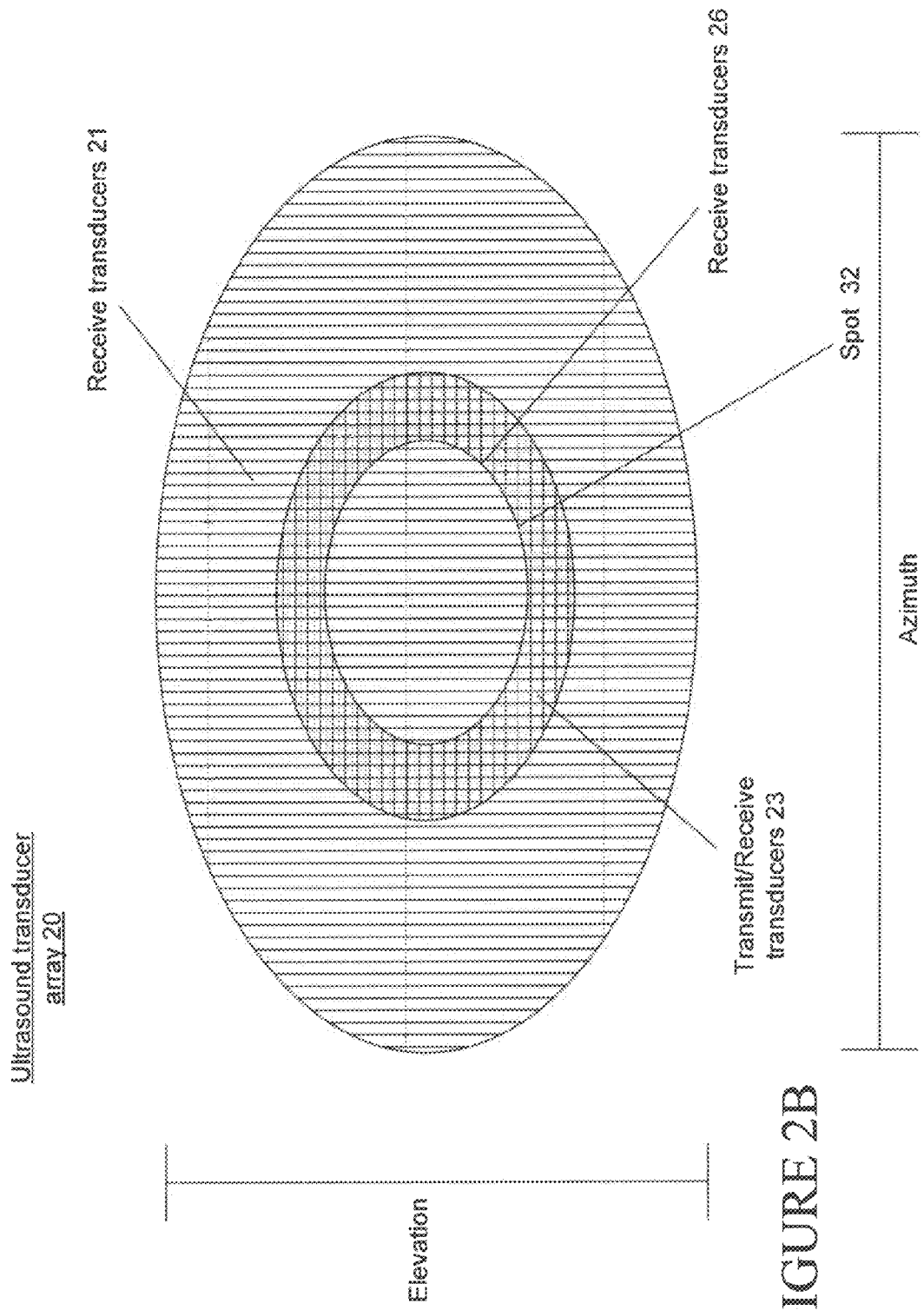
FIG. 2B illustrates an ultrasound transducer array according to an embodiment of the present invention having an elliptical aperture and an elliptical spot and having a receive only area, a transmit/receive area and a receive only spot area.

FIG. 2B illustrates an ultrasound transducer array 20 having an elliptical spot 32 and that includes receive-only elements 21, transmit/receive elements 23 and receive-only elements 26 in the spot area 32. The receive-only elements 21 are transducers that exclusively receive reflected ultrasound reverberations. The receive-only elements 26 in the spot 32 also exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

Embodiment 3

Circular Spot

Figure 1C:
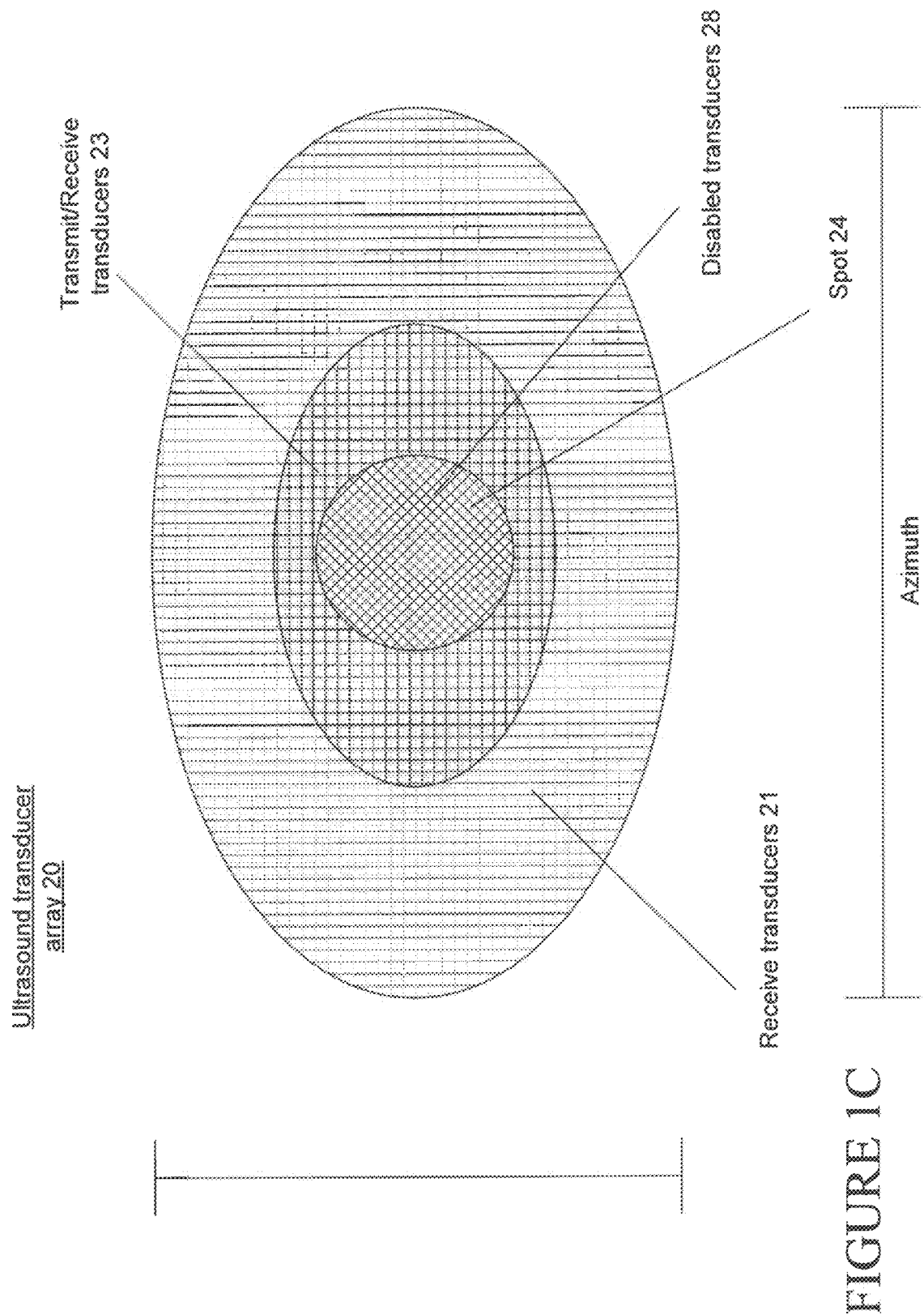
FIG. 1C illustrates an ultrasound transducer array according to an embodiment of the present invention having an elliptical aperture and a circular spot and having a receive only area, a transmit/receive area and a disabled spot area.

FIG. 1C illustrates an ultrasound transducer array 20 having a circular spot 24 and that includes receive-only elements 21, transmit/receive elements 23 and disabled elements 28 in the spot area 24. The receive-only elements 21 are transducers that exclusively receive reflected ultrasound reverberations. The disabled elements 28 in the spot 24 are unable to transmit or to receive and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 2C:
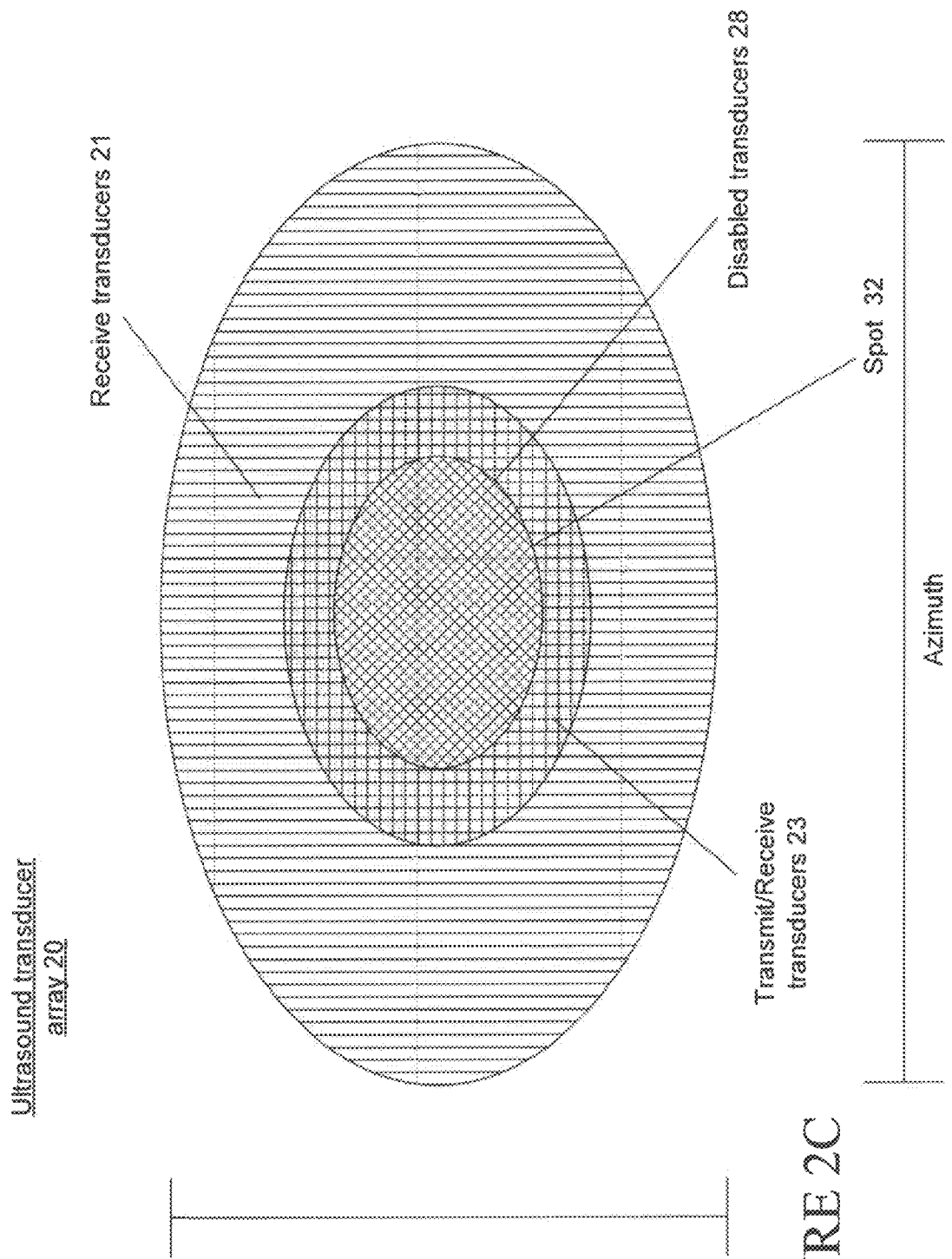
FIG. 2C illustrates an ultrasound transducer array according to an embodiment of the present invention having an elliptical aperture and an elliptical spot and having a receive only area, a transmit/receive area and a disabled spot area.

FIG. 2C illustrates an ultrasound transducer array 20 having an elliptical spot 32 and that includes receive-only elements 21, transmit/receive elements 23 and disabled elements 28 in the spot area 32. The receive-only elements 21 are transducers that exclusively receive reflected ultrasound reverberations. The disabled elements 28 in the spot 32 are unable to transmit or to receive and the transmit/receive elements 23 are transducer elements that can both transmit and receive the ultrasonic waves and can be switched such that the transmit/receive elements 23 can perform the function of a transmit element or the function of a receive element.

Dynamic Spot

Figure 3A:
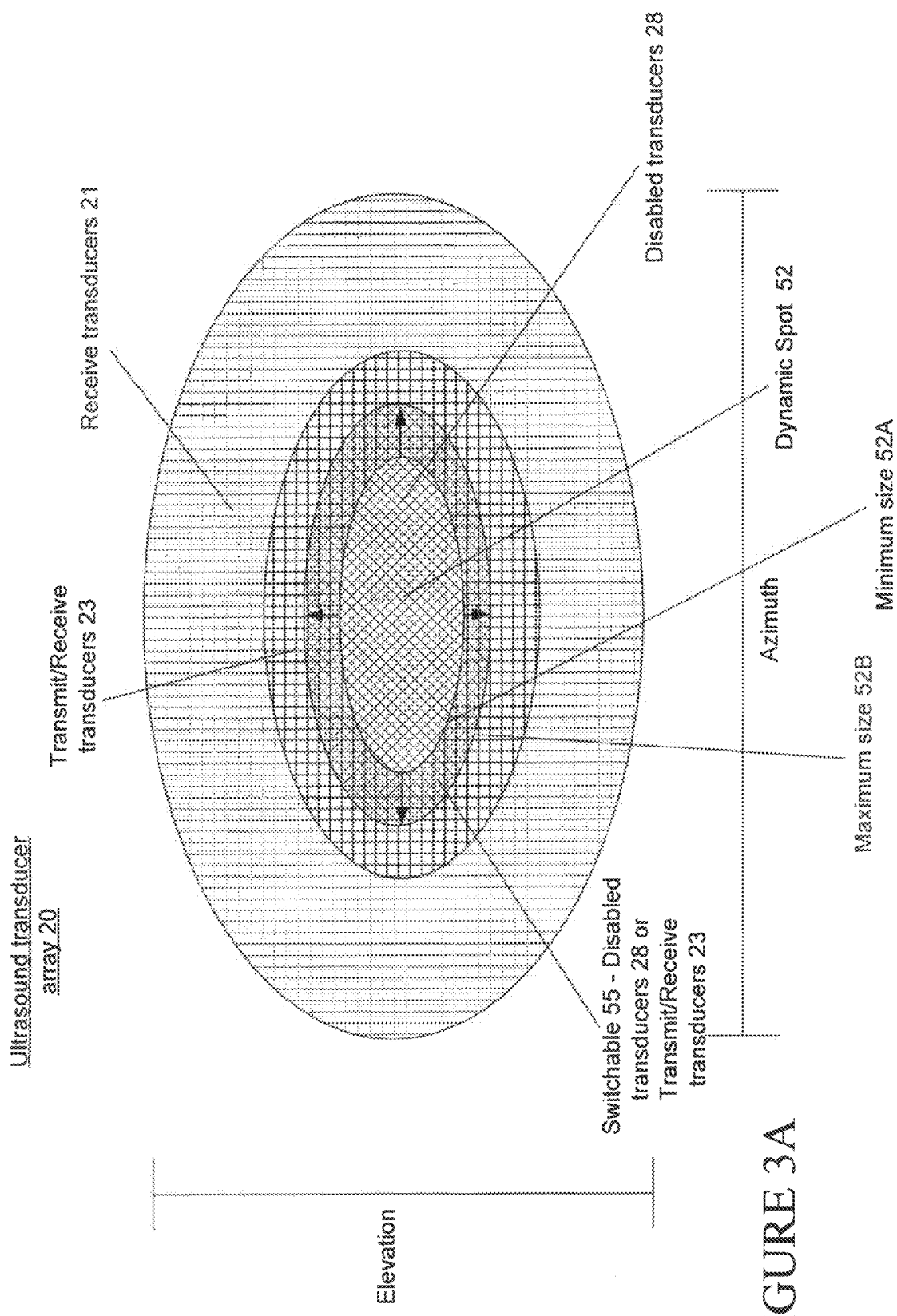
FIG. 3A illustrates an ultrasound transducer array according to an embodiment of the present invention having an elliptical aperture and a dynamic spot and having a receive only area, a transmit/receive area, a disabled spot area, and a fourth area between the disabled spot area and the transmit/receive area which is switchable between being disabled and transmit/receive.

FIG. 3A illustrates an ultrasound transducer array 20 having a dynamic spot 52 and that includes receive-only elements 21, transmit/receive elements 23 and disabled elements 28. The receive-only elements 21 are transducers that exclusively receive reflected ultrasound reverberations. The disabled elements 28 in the spot 52 are unable to transmit or to receive and the transmit/receive elements 23 are transducer elements that can both transmit and receive the ultrasonic waves and can be switched such that the transmit/receive elements 23 can perform the function of a transmit element or the function of a receive element.

The dynamic spot 52 has a maximum size 52B and a minimum size 52A, the maximum and minimum sizes shown in FIG. 3A are exemplary, the maximum and minimum sizes of the dynamic spot 52 can each be much larger or smaller.

The area between the maximum size 52B and the minimum size 52A includes elements 55 which a switchable between disabled transistors 28 and transmit/receive transistors 23. The spot 52 can expand to the maximum size 52B or shrink to the minimum size 52A by using the switchable elements 55. Thus, the dynamic spot 52 can grow smaller or larger or change shape (for example, from circle to ellipse, or larger and smaller) based on the needs of the focusing characteristics and image depth related requirements. Control of the switching of the switchable elements 55 can be performed by a main processing unit or by other electronic circuitry in the probe.

Thus, the enabling and disabling of elements can be performed using local enabling and disabling calculations performed locally to the array. Alternatively, the enabling and disabling of the switchable elements 55 can be performed in the main processing unit. Thus, the switching process takes into account the focus resulting from the execution of the function of the ultrasound transducer array and the shape of the spot 52. For example, the present architecture can take into account image depth, transmit focus and other spot specific parameters to produce a certain sized/shaped spot by disabling elements accordingly. In addition, the switching logic can be updated while the beam is being dynamically focused from near to far field. Thus, the size and shape of the dynamic spot 52 can be precisely controlled to provide a more precise and accurate image in the near-field even during 2D scans.

Embodiment 4

Figure 3B:
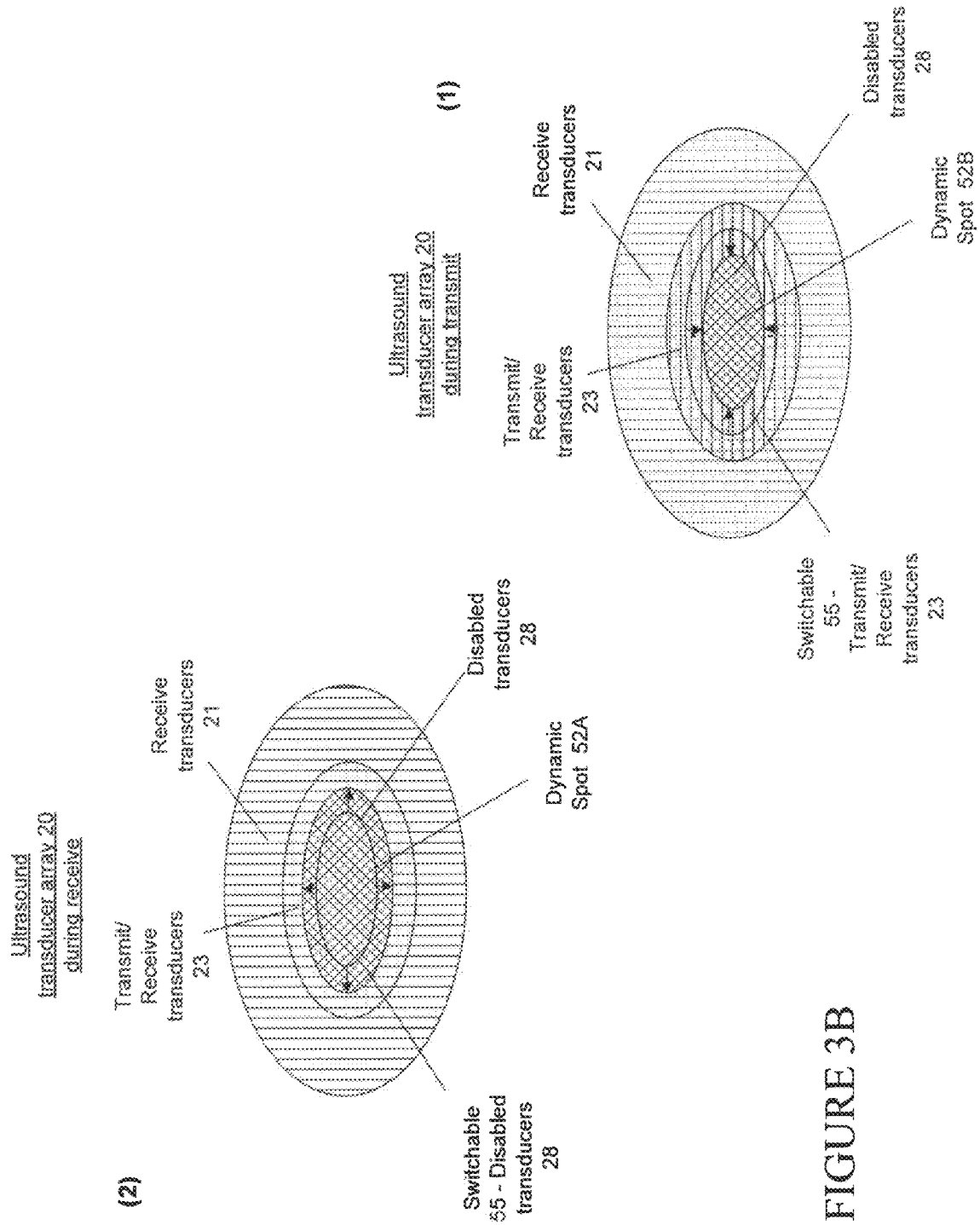
FIG. 3B illustrates an ultrasound transducer array according to an embodiment of the present invention having different spot sizes during receive and during transmit, the ultrasound transducer array having an elliptical aperture and a dynamic spot having a receive only area, a transmit/receive area, a disabled spot area, and a fourth area between the disabled spot area and the transmit/receive area which is switchable between being disabled and transmit/receive.

FIG. 3B illustrates an ultrasound transducer array according to an embodiment of the present invention having different dynamic spot sizes during receive and during transmit. The transducer arrays shown in FIG. 3B have the structure as the transducer array in FIG. 3A. However, in the example shown in FIG. 3B, when the transducer array 20 is transmitting the ultrasound signal as is shown in FIG. 3B-(1), the receive transducers 21 are inactive, the receive/transmit transducers 23 are performing a transmit function, the transducers in the switchable area 55 are set to transmit, and the transducers in the spot area 28 are disabled. The dynamic spot 52B thus has a first size during transmit which corresponds to the size of the disabled spot area 28. In contrast, in FIG. 3B-(2)

there is shown an example corresponding to when the transducer array is in receive mode. In the example of receive mode, the receive transducers 21 are active, the receive/transmit transducers 23 are performing a receive function, the transducers in the switchable area 55 are set to disabled, and the transducers in the spot area 28 are disabled. Thus, the dynamic spot 52A has a second size during receive which corresponds to a combination of the size of the disabled spot area 28 and the switchable area 55. This example can also function when the spot area is transmit-only, receive-only and transmit/receive.

Figure 3C:
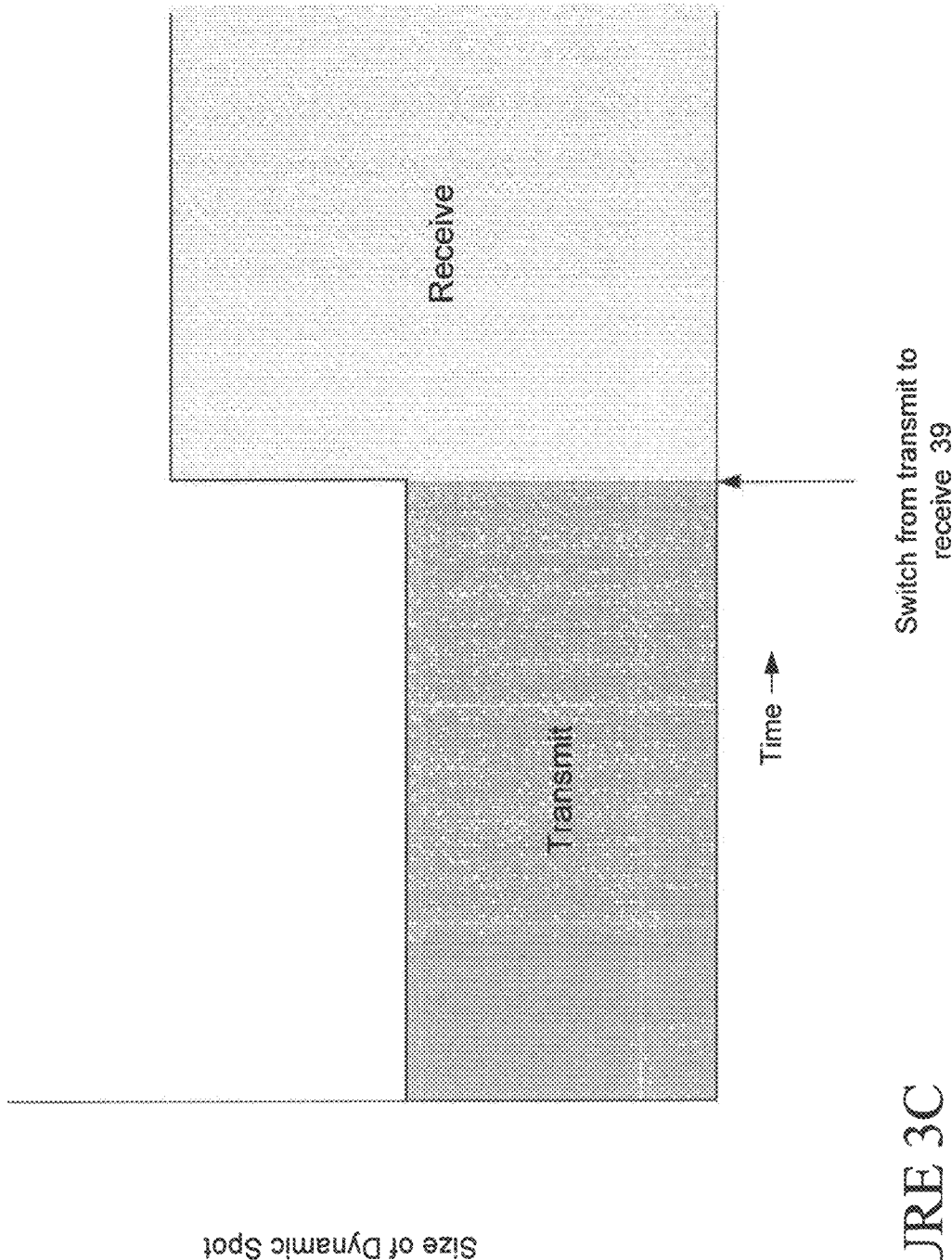
FIG. 3C illustrates a graph showing the size of the dynamic spot over time according to an embodiment of the present invention in which the size of the spot during transmit is different than the size of the spot during receive.

FIG. 3C illustrates a graph showing the size of the dynamic spot over time when the size of the spot during transmit is different than the size of the spot during receive. As is shown in FIG. 3C, the size of the dynamic spot 52 changes when the transducer array is switched 39 from transmit to receive. It should be noted that the example shown in FIG. 3C illustrates that the size of the dynamic spot during transmit is smaller than the size of the dynamic spot during receive, however, the size of the dynamic spot during transmit can also be smaller than or equal to or larger than (in a different embodiment) the size of the dynamic spot during receive.

Embodiment 5

Figure 4A:
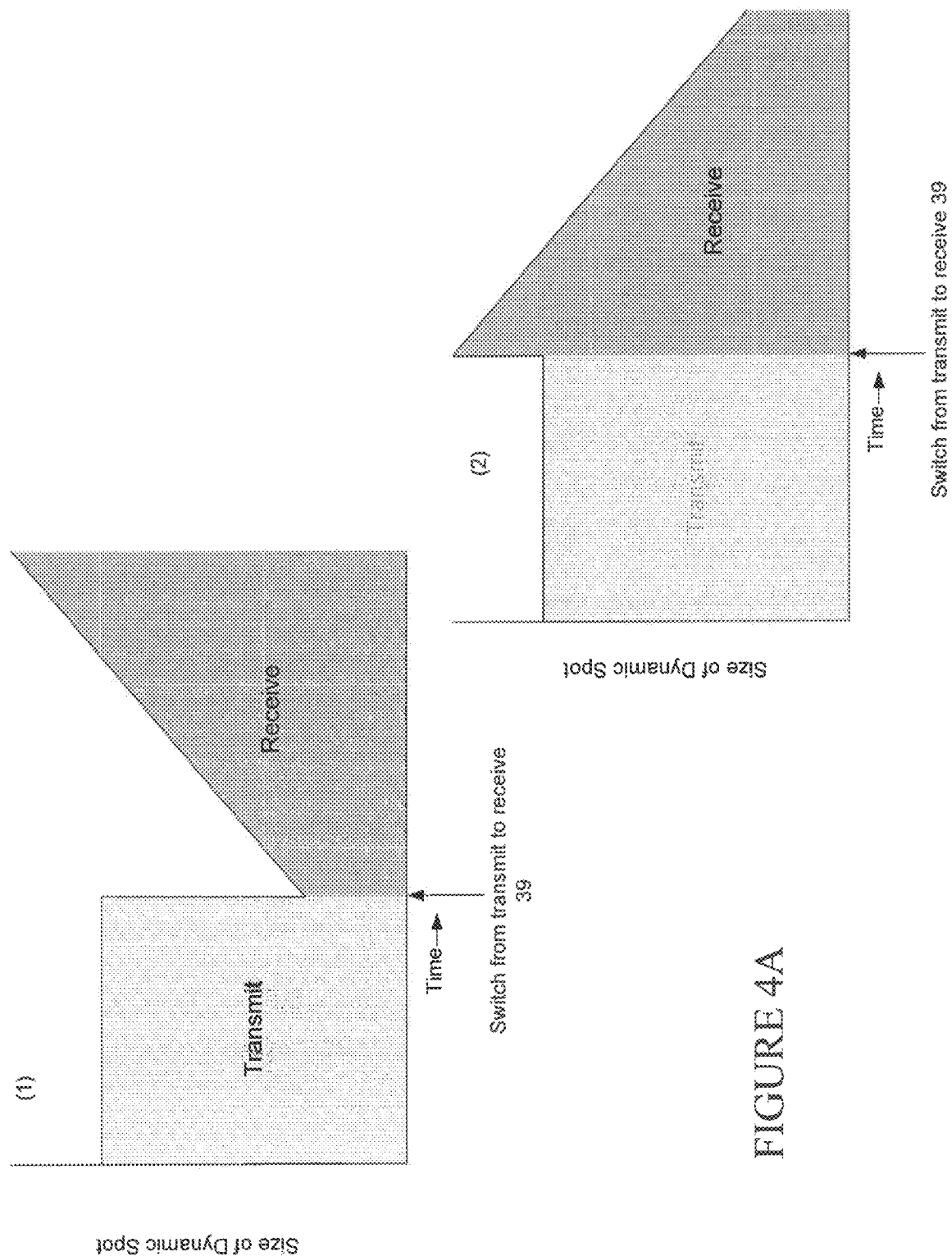
FIG. 4A illustrates graphs showing the size of the dynamic spot over time according to an embodiment of the present invention in which the size of the spot during transmit is different than the size of the spot during receive and the size of the spot during receive is dynamic.

The ultrasound transducer array having the structure shown in FIG. 3A (dynamic spot 52 and that includes receive-only elements 21, transmit/receive elements 23 and disabled elements 28) can be used in the example shown in FIG. 4A. FIG. 4A illustrates graphs (1) and (2) showing the size of the dynamic spot over time when the size of the spot during transmit is different than the size of the spot during receive. In addition, FIG. 4A illustrates that during receive the size of the dynamic spot 52A can change during the reception of the ultrasonic beam. As is shown in FIG. 4A, the size of the dynamic spot 52A changes when the transducer array is switched 39 from transmit to receive. In addition, as is shown in FIG. 4A-(1), the size of the dynamic spot 52A may increase as the reception of the ultrasonic beam is received. It should be noted that the dynamic spot 52A can also decrease during the reception of the ultrasonic beam as is shown in FIG. 4A-(2). In addition, the size of the dynamic spot 52A can increase and decrease or decrease and increase multiple times during the reception of the ultrasonic beam.

Embodiment 6

Figure 4B:
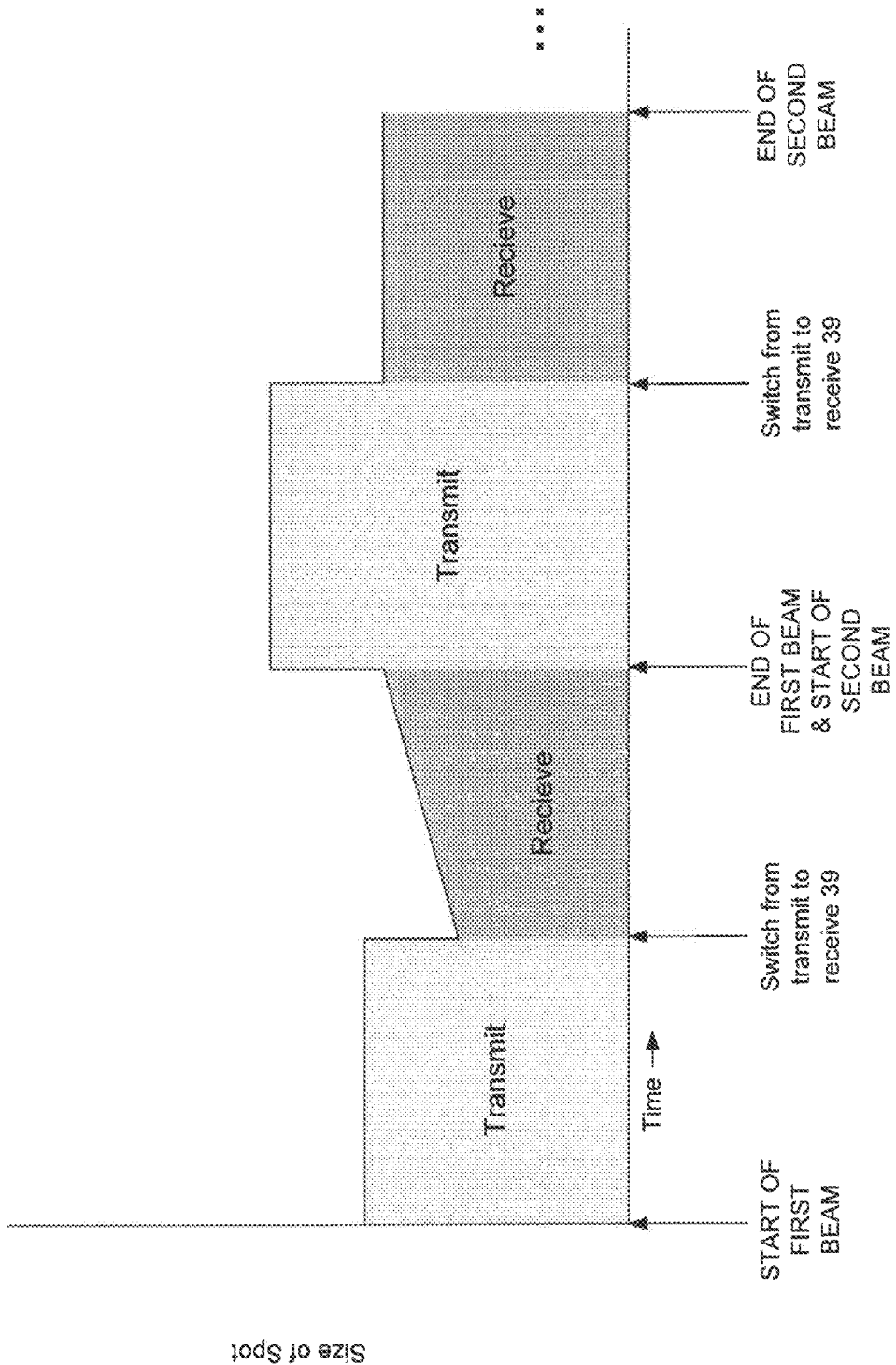
FIG. 4B illustrates a graph showing the size of the dynamic spot over time according to an embodiment of the present invention in which the size of the spot during transmit is different than the size of the spot during receive and the size of the spot for transmit and receive is dynamic from beam to beam.

The ultrasound transducer array having the structure shown in FIG. 3A (dynamic spot 52 and that includes receive-only elements 21, transmit/receive elements 23 and disabled elements 28) can be used in the example shown in FIG. 4B. FIG. 4B illustrates a graph showing the size of the dynamic spot over time when the size of the spot during transmit is different than the size of the spot during receive. In addition, FIG. 4B illustrates that during receive the size of the dynamic spot 52 can change during the reception of the ultrasonic beam. Moreover, FIG. 4B illustrates that the size of the dynamic spot 52 can change from beam to beam. As is shown in FIG. 4B, the size of the dynamic spot 52 changes when the transducer array is switched 39 from transmit to receive for each beam (first and second beam). The example shown in FIG. 4B illustrates two beams; however, the example shown in FIG. 4B is applicable to a plurality of beams. In addition, as is shown in FIG. 4B, the size of the dynamic spot 52 increases as the reception of the first ultrasonic beam is received. It should be noted that the dynamic spot 52 can increase or decrease or stay the same during the reception of the first ultrasonic beam, second ultrasonic beam or any ultrasonic beam thereafter. In addition, the size of the dynamic spot can increase and decrease or decrease and increase multiple times during the reception of each of the ultrasonic beams. Furthermore, the size of the dynamic spot 52 during the transmit first beam and receive first beam can be different from the size of the dynamic spot 52 during the transmit second beam and receive second beam, respectively.

Embodiment 7

Circular Spot

Figure 5A:
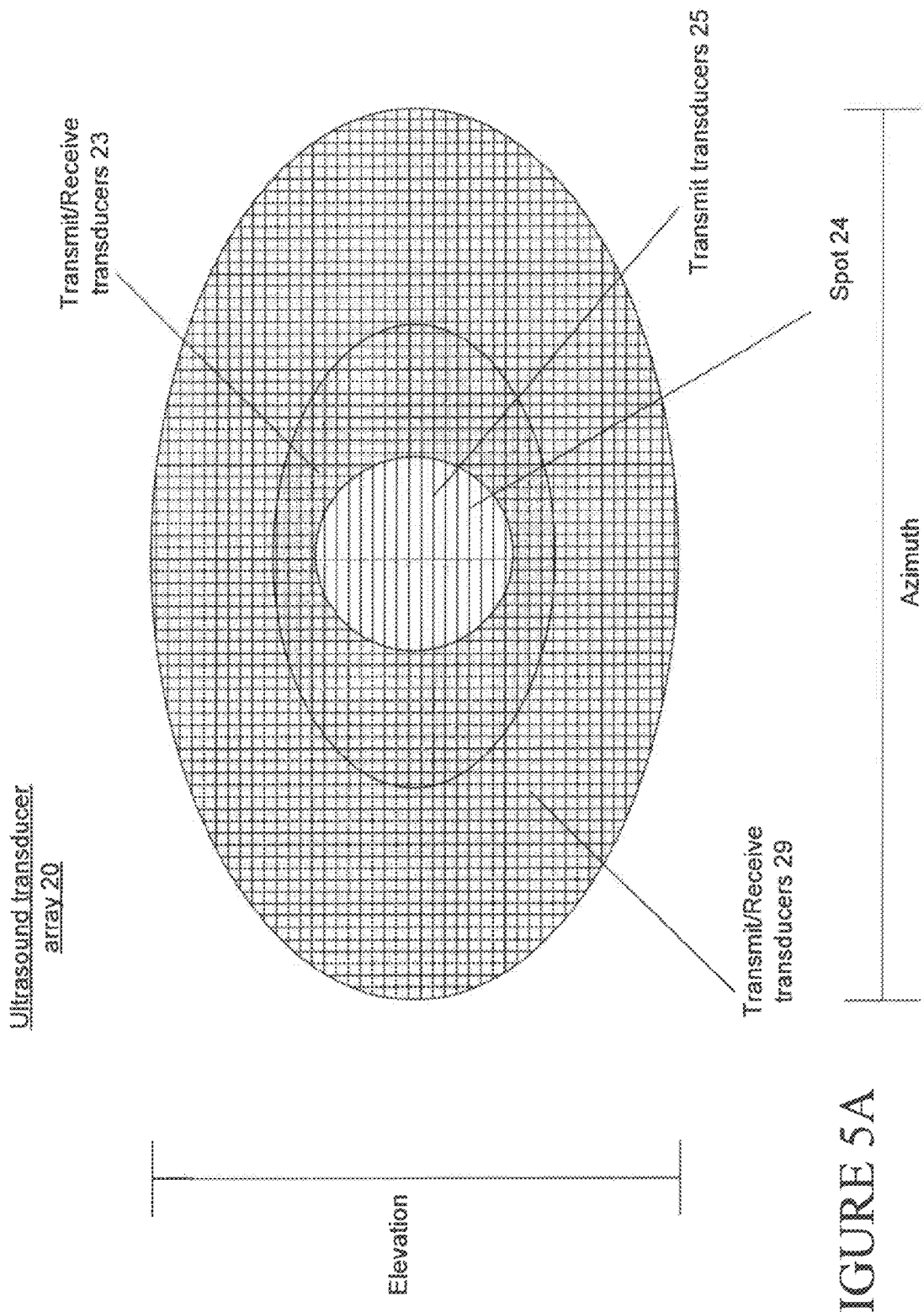
FIG. 5A illustrates an ultrasound transducer array according to an embodiment of the present invention having an elliptical aperture and a circular spot and having a first transmit/receive area, a second transmit/receive area and a transmit only spot area.

FIG. 5A illustrates an ultrasound transducer array 20 having a circular spot 24 and that includes transmit/receive elements 29, transmit/receive elements 23 and transmit-only elements 25 in the spot area 24. The transmit/receive elements 29 are transducers that can both transmit and receive the ultrasonic waves and can be switched such that the transmit/receive elements 29 can perform the function of a transmit element or the function of a receive element. The transmit-only elements 25 in the spot 24 exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 6A:
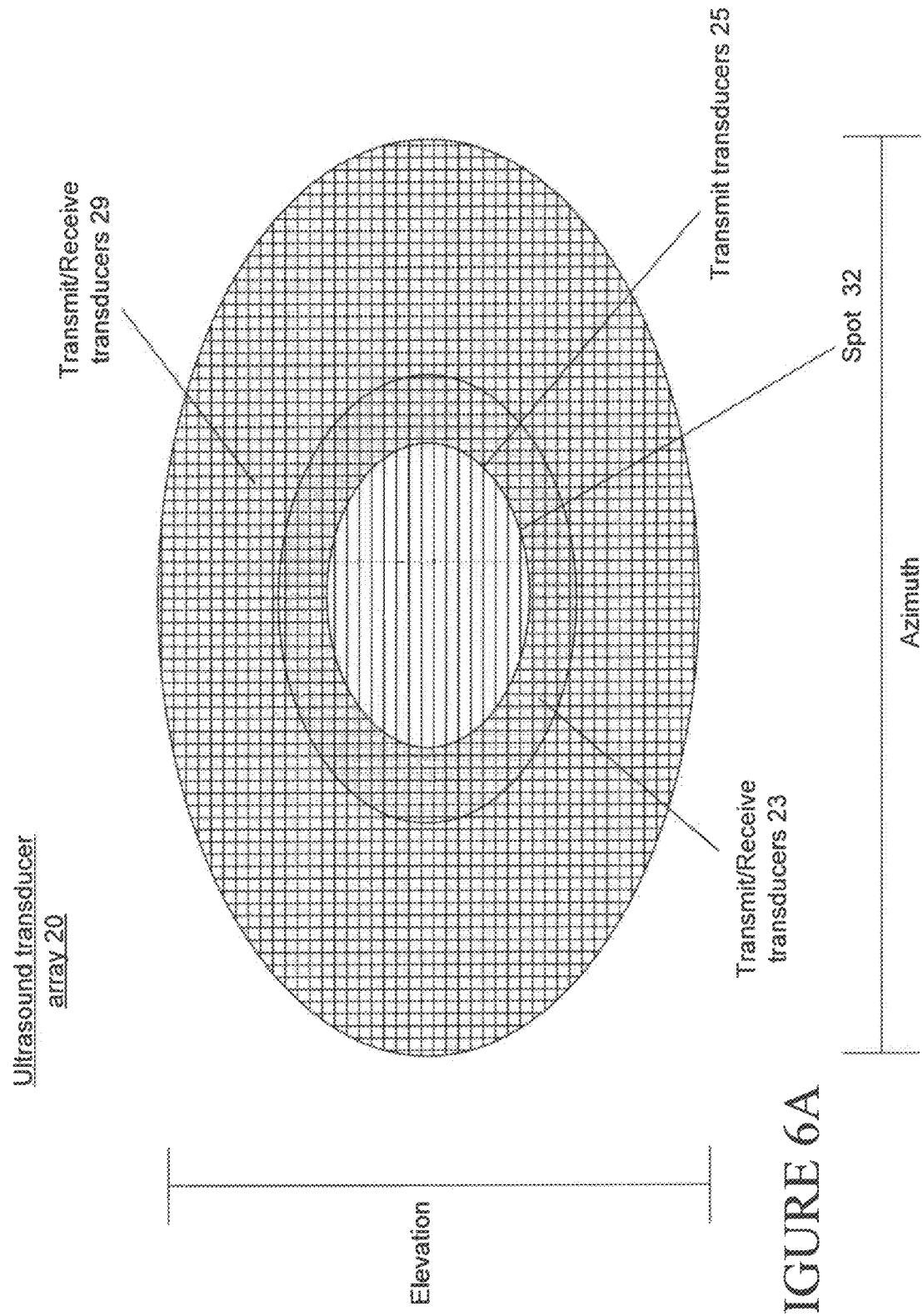
FIG. 6A illustrates an ultrasound transducer array according to an embodiment of the present invention having an elliptical aperture and an elliptical spot and having a first transmit/receive area, a second transmit/receive area and an elliptical transmit only spot area.

FIG. 6A illustrates an ultrasound transducer array 20 having an elliptical spot 32 and that includes transmit/receive elements 29, transmit/receive elements 23 and transmit-only elements 25 in the spot area 32. The transmit/receive elements 29 are transducers that can both transmit and receive the ultrasonic waves and can be switched such that the transmit/receive elements 29 can perform the function of a transmit element or the function of a receive element. The transmit-only elements 25 in the spot 32 exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

Embodiment 8

Circular Spot

Figure 5B:
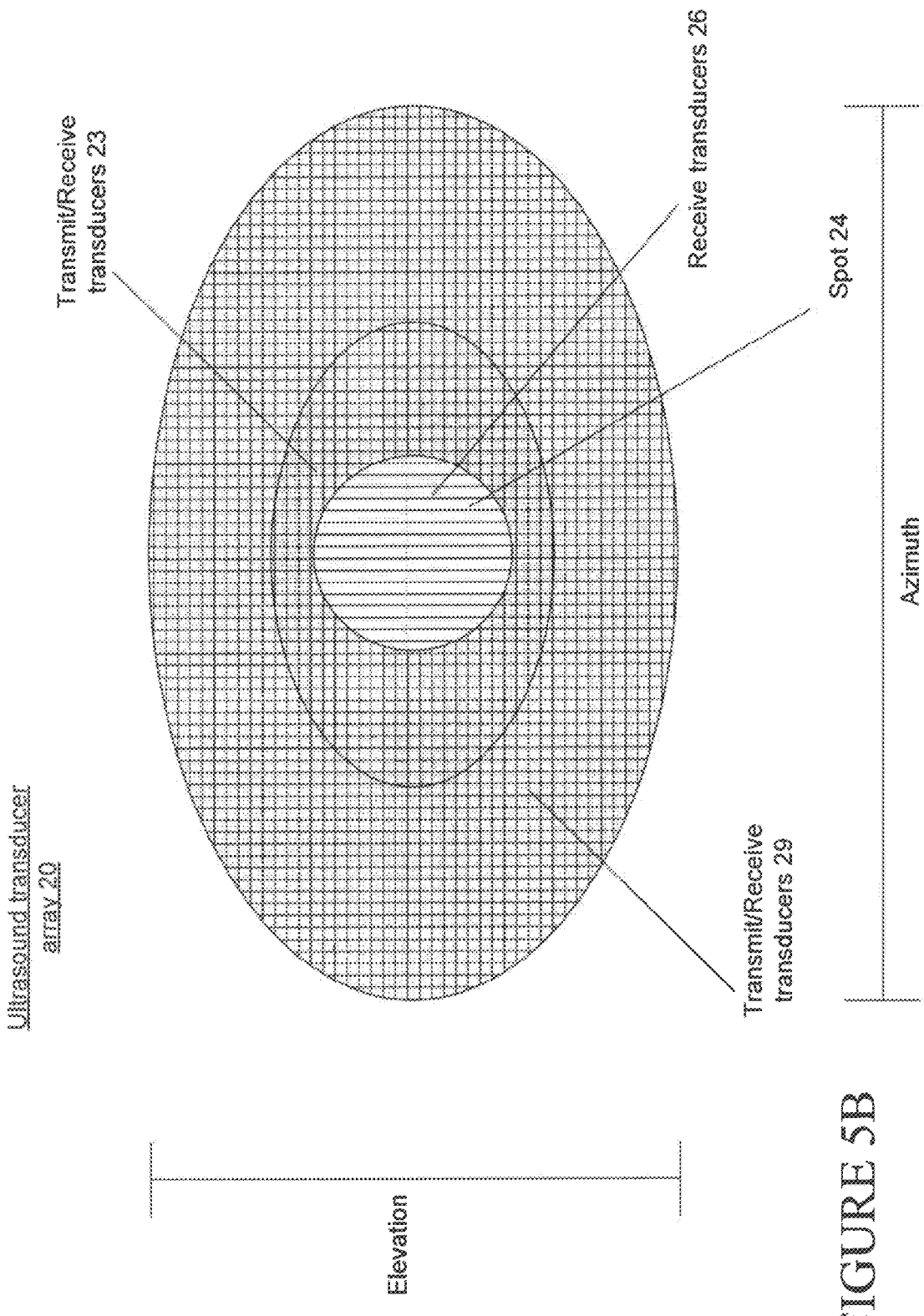
FIG. 5B illustrates an ultrasound transducer array according to an embodiment of the present invention having an elliptical aperture and a circular spot and having a first transmit/receive area, a second transmit/receive area and a receive only spot area.

FIG. 5B illustrates an ultrasound transducer array 20 having a circular spot 24 and that includes transmit/receive elements 29, transmit/receive elements 23 and receive-only elements 26 in the spot area 24. The transmit/receive elements 29 are transducers that can both transmit and receive the ultrasonic waves and can be switched such that the transmit/receive elements 29 can perform the function of a transmit element or the function of a receive element. The receive-only elements 26 in the spot 24 also exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 6B:
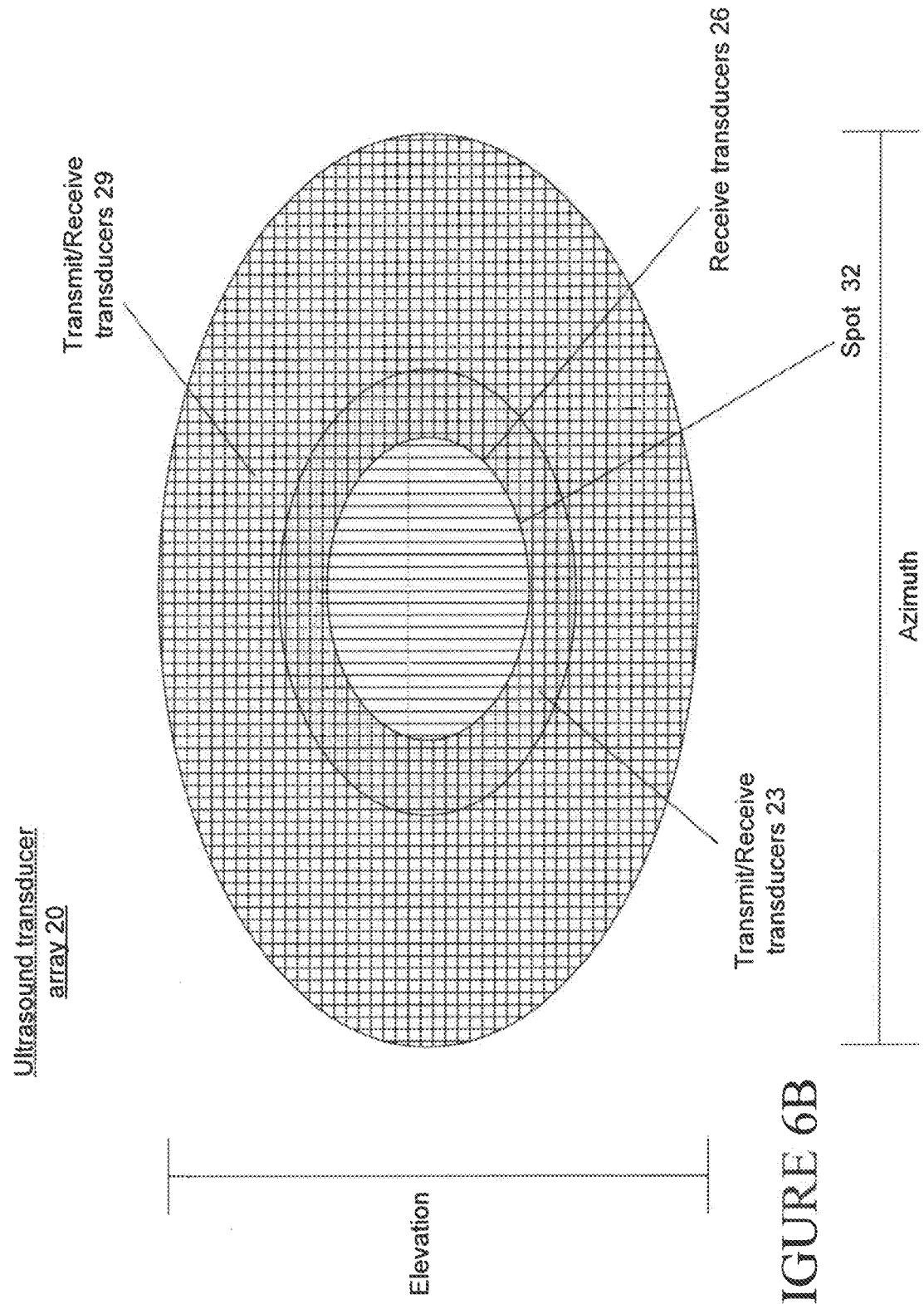
FIG. 6B illustrates an ultrasound transducer array according to an embodiment of the present invention having an elliptical aperture and an elliptical spot and having a first transmit/receive area, a second transmit/receive area and an elliptical receive only spot area.

FIG. 6B illustrates an ultrasound transducer array 20 having an elliptical spot 32 and that includes transmit/receive elements 29, transmit/receive elements 23 and receive-only elements 26 in the spot area 32. The transmit/receive elements 29 are transducers that can both transmit and receive the ultrasonic waves and can be switched such that the transmit/receive elements 29 can perform the function of a transmit element or the function of a receive element. The receive-only elements 26 in the spot 32 also exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

Embodiment 9

Circular Spot

Figure 5C:
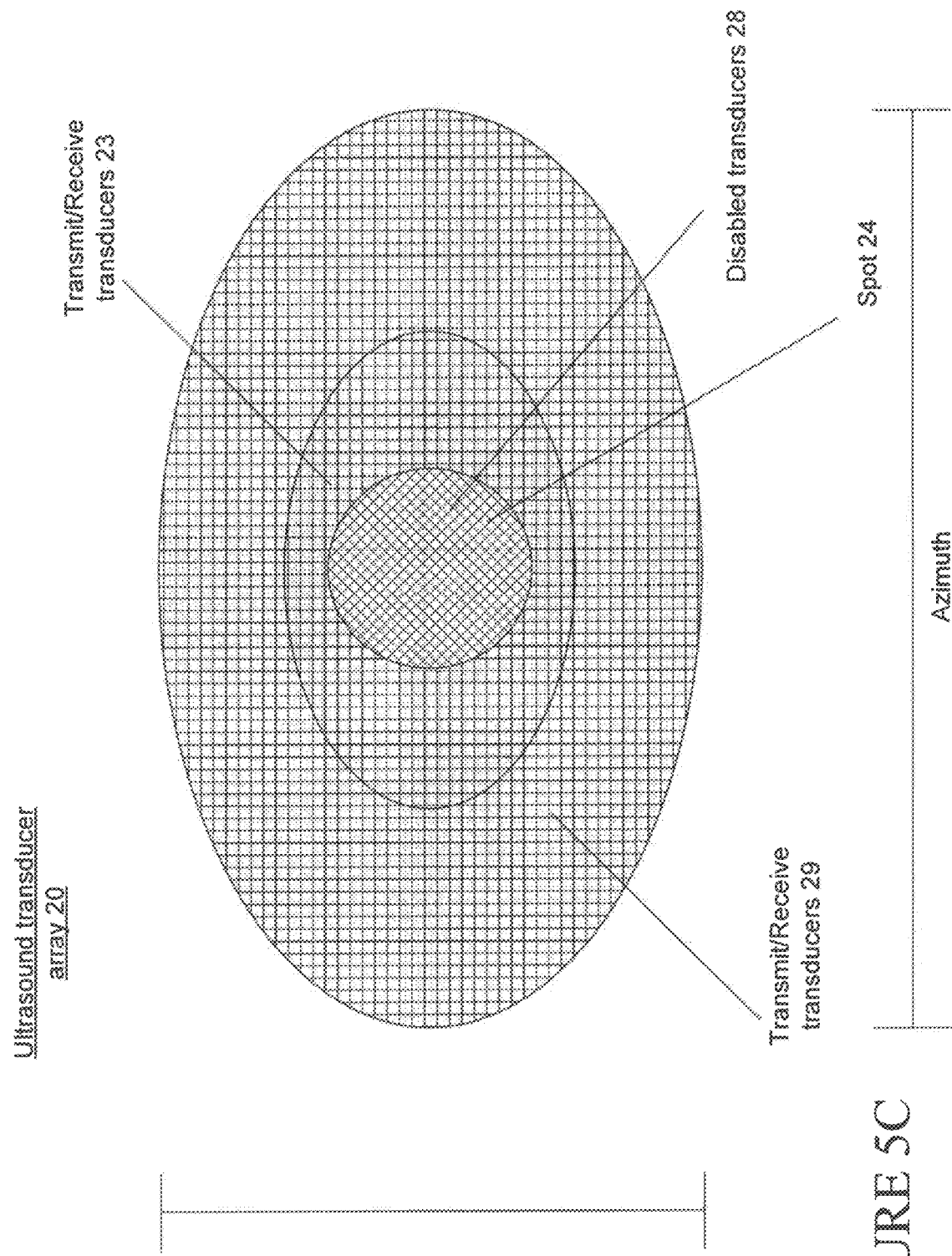
FIG. 5C illustrates an ultrasound transducer array according to an embodiment of the present invention having an elliptical aperture and a circular spot and having a first transmit/receive area, a second transmit/receive area and a disabled spot area.

FIG. 5C illustrates an ultrasound transducer array 20 having a circular spot 24 and that includes transmit/receive elements 29, transmit/receive elements 23 and disabled elements 28 in the spot area 24. The transmit/receive elements 29 are transducers that can both transmit and receive the ultrasonic waves and can be switched such that the transmit/receive elements 29 can perform the function of a transmit element or the function of a receive element. The disabled elements 28 in the spot 24 are unable to transmit or to receive and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 6C:
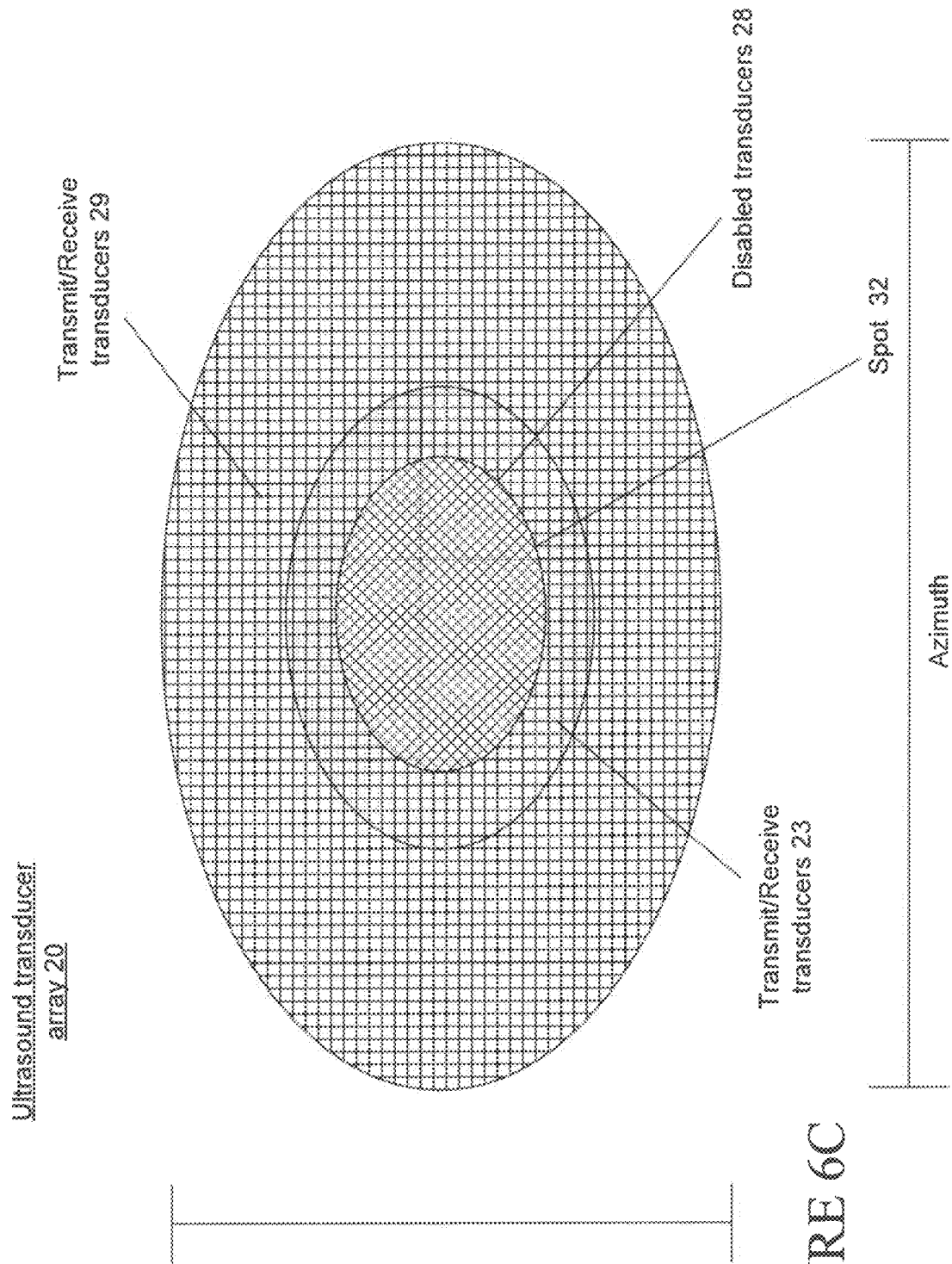
FIG. 6C illustrates an ultrasound transducer array according to an embodiment of the present invention having an elliptical aperture and an elliptical spot and having a first transmit/receive area, a second transmit/receive area and an elliptical disabled spot area.

FIG. 6C illustrates an ultrasound transducer array 20 having an elliptical spot 32 and that includes transmit/receive elements 29, transmit/receive elements 23 and disabled elements 28 in the spot area 32. The transmit/receive elements 29 are transducers that can both transmit and receive the ultrasonic waves and can be switched such that the transmit/receive elements 29 can perform the function of a transmit element or the function of a receive element. The disabled elements 28 in the spot 32 are unable to transmit or to receive and the transmit/receive elements 23 are transducer elements that can both transmit and receive the ultrasonic waves and can be switched such that the transmit/receive elements 23 can perform the function of a transmit element or the function of a receive element.

Embodiment 10

Figure 7A:
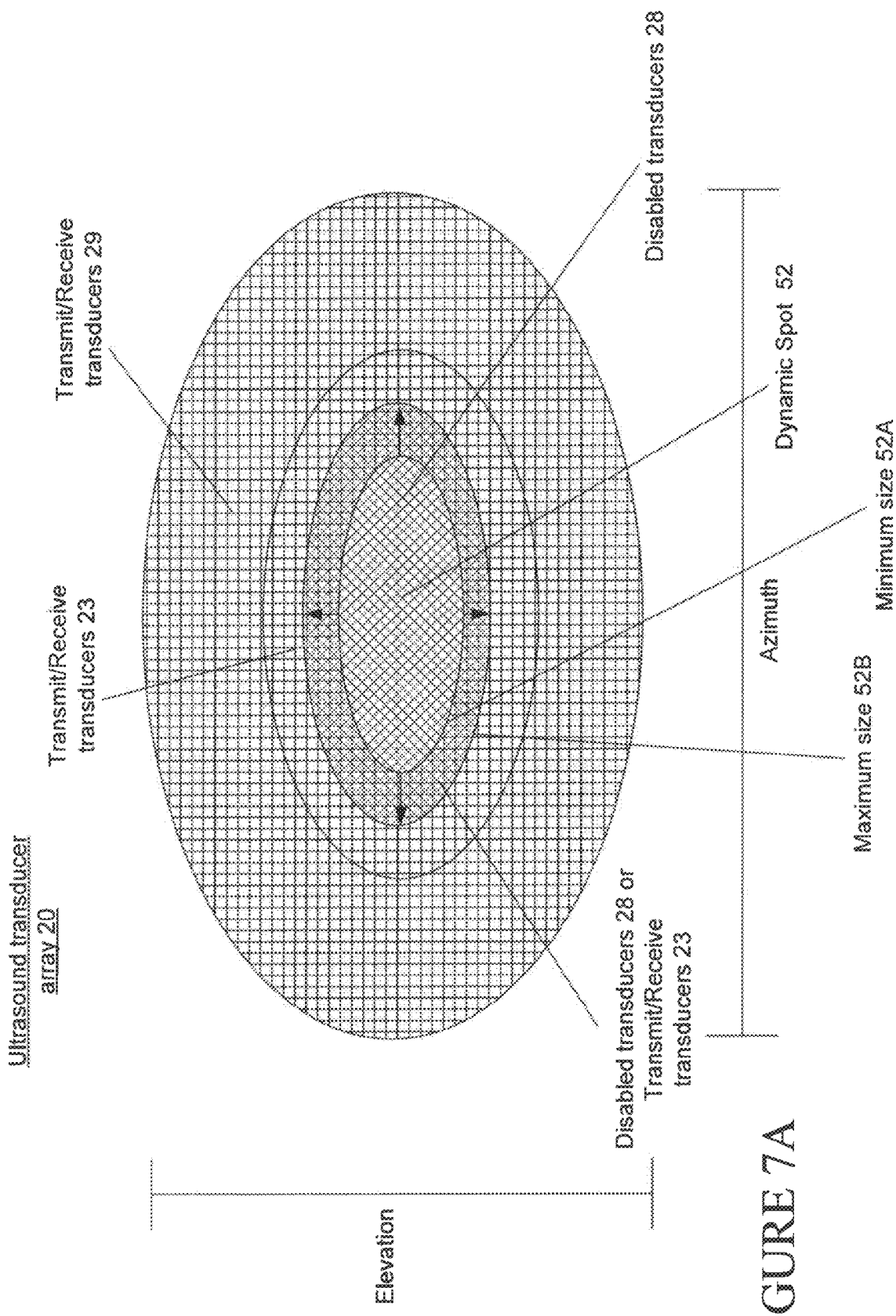
FIG. 7A illustrates an ultrasound transducer array according to an embodiment of the present invention having an elliptical aperture and a dynamic spot and having a first transmit/receive area, a second transmit/receive area, a disabled spot area, and a fourth area between the disabled spot area and the second transmit/receive area which is switchable between being disabled and transmit/receive.

FIG. 7A illustrates an ultrasound transducer array 20 having a dynamic spot 52 and that includes transmit/receive elements 29, transmit/receive elements 23 and disabled elements 28. The transmit/receive elements 29 are transducers that can both transmit and receive the ultrasonic waves and can be switched such that the transmit/receive elements 29 can perform the function of a transmit element or the function of a receive element. The disabled elements 28 in the spot 32 are unable to transmit or to receive and the transmit/receive elements 23 are transducer elements that can both transmit and receive the ultrasonic waves and can be switched such that the transmit/receive elements 23 can perform the function of a transmit element or the function of a receive element.

Figure 8:
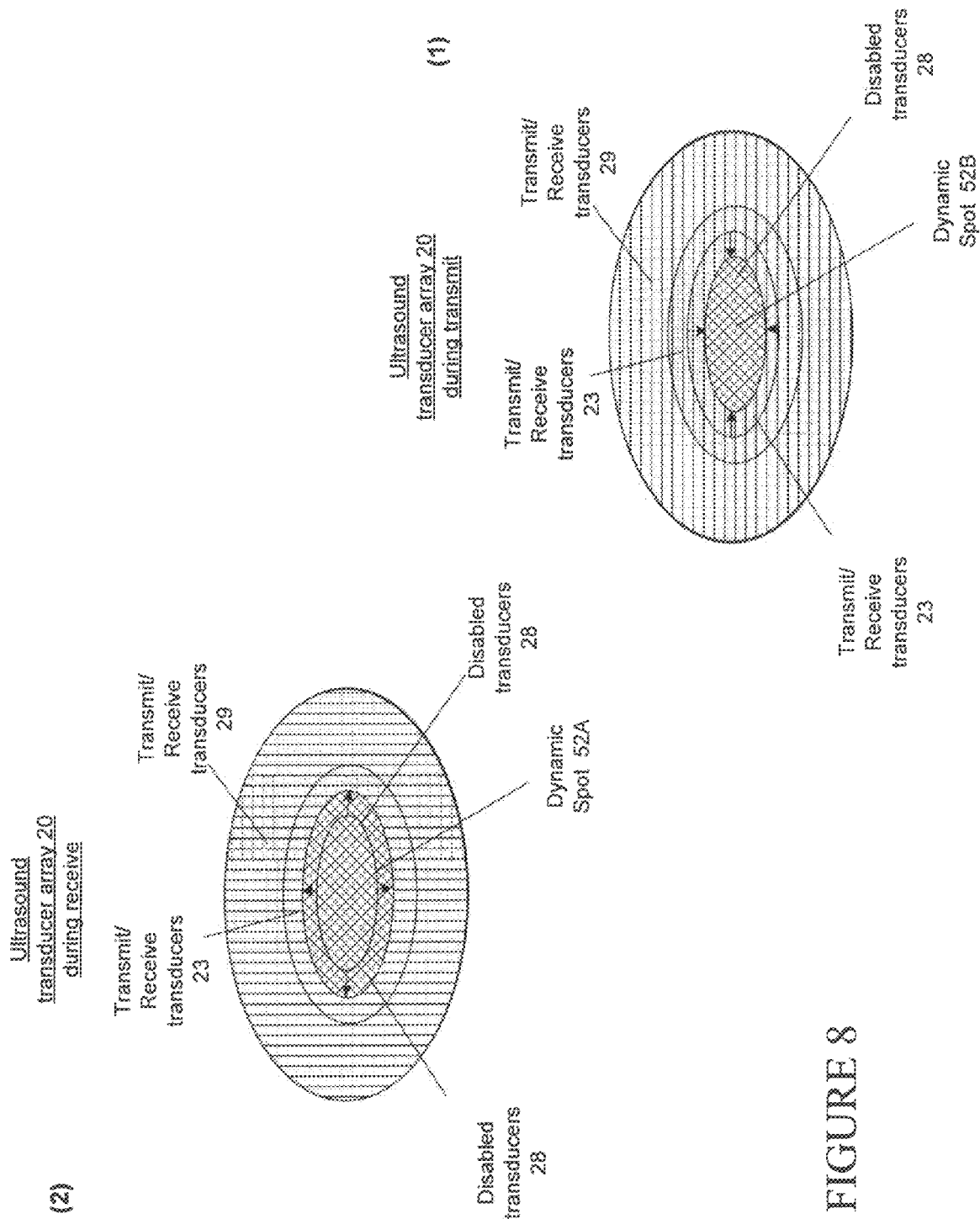
FIG. 8 illustrates an ultrasound transducer array according to an embodiment of the present invention having different dynamic spot sizes during receive and during transmit, the ultrasound transducer array having an elliptical aperture and a dynamic spot having a first transmit/receive area, a second transmit/receive area, a disabled spot area, and a fourth area between the disabled spot area and the second transmit/receive area which is switchable between being disabled and transmit/receive.

FIG. 8 illustrates an ultrasound transducer array according to an embodiment of the present invention having different dynamic spot sizes during receive and during transmit. The transducer arrays shown in FIG. 8 have the structure as the transducer array in FIG. 7A. However, in the example shown in FIG. 8, when the transducer array 20 is transmitting the ultrasound signal as is shown in FIG. 8-(1), the transmit/receive transducers 29 are set to transmit, the receive/transmit transducers 23 are also set to transmit and are performing a transmit function, the transducers in the switchable area 55 are set to transmit, and the transducers in the spot area 28 are disabled. The dynamic spot 52B thus has a first size during transmit which corresponds to the size of the disabled spot area 28. In contrast, in FIG. 8-(2) there is shown an example corresponding to when the transducer array is in receive mode. In the example of receive mode, the transmit/receive transducers 29 are set to receive, the receive/transmit transducers 23 are also set to receive and are performing a receive function, the transducers in the switchable area 55A are set to disabled, and the transducers in the spot area 28 are disabled. Thus, the dynamic spot 52 has a second size during receive which corresponds to a combination of the size of the disabled spot area 28 and the switchable area 55. This example can also function when the spot area is transmit-only, receive-only and transmit/receive. Thus, as is shown in FIG. 3C, the dynamic spot 52 may have different sizes during transmit and receive.

Embodiment 11

The ultrasound transducer array having the structure shown in FIG. 7A (dynamic spot 52 and that includes transmit/receive elements 29, transmit/receive elements 23 and disabled elements 28) can be used in the example shown in FIG. 4A. As is noted above, FIG. 4A illustrates graphs (1) and (2) showing the size of the dynamic spot over time when the size of the spot during transmit is different than the size of the spot during receive. In addition, FIG. 4A illustrates that during receive, the size of the dynamic spot 52A can change (is dynamic) during the reception of the ultrasonic beam. Thus, the dynamic spot 52A/B shown in FIG. 7A can have different sizes during transmit and receive and the size of the dynamic spot 52A can change during receive.

Embodiment 12

The ultrasound transducer array having the structure shown in FIG. 7A (dynamic spot 52 and that includes transmit/receive elements 29, transmit/receive elements 23 and disabled elements 28) can be used in the example shown in FIG. 4B. FIG. 4B illustrates a graph showing the size of the dynamic spot over time when the size of the spot during transmit is different than the size of the spot during receive. In addition, FIG. 4B illustrates that during receive the size of the dynamic spot 52 can change during the reception of the ultrasonic beam. Moreover, FIG. 4B illustrates that the size of the dynamic spot 52 can change from beam to beam. Thus, the dynamic spot 52 shown in FIG. 7A can have different sizes during transmit and receive, the size of the dynamic spot 52 can change during receive, and the size of the dynamic spot 52 can change from beam to beam.

Embodiment 13

Circular Spot

Figure 9A:
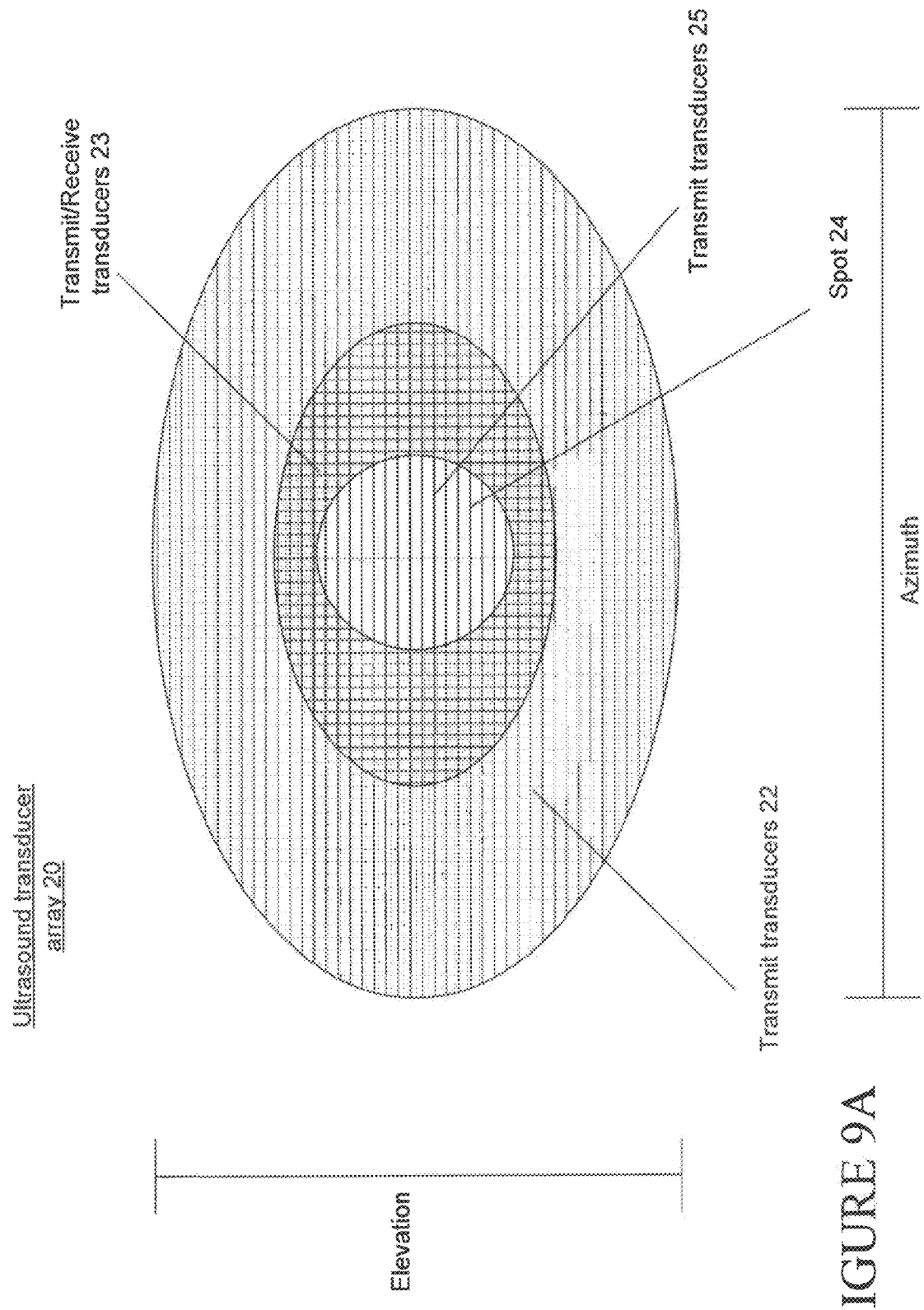
FIG. 9A illustrates an ultrasound transducer array according to an embodiment of the present invention having an elliptical aperture and a circular spot and having a transmit only area, a transmit/receive area and a transmit only spot area.

FIG. 9A illustrates an ultrasound transducer array 20 having a circular spot 24 and that includes transmit-only elements 22, transmit/receive elements 23 and transmit-only elements 25 in the spot area 24. The transmit-only elements 22 are transducers that exclusively transmit the ultrasonic waves. The transmit-only elements 25 in the spot 24 also exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 10A:
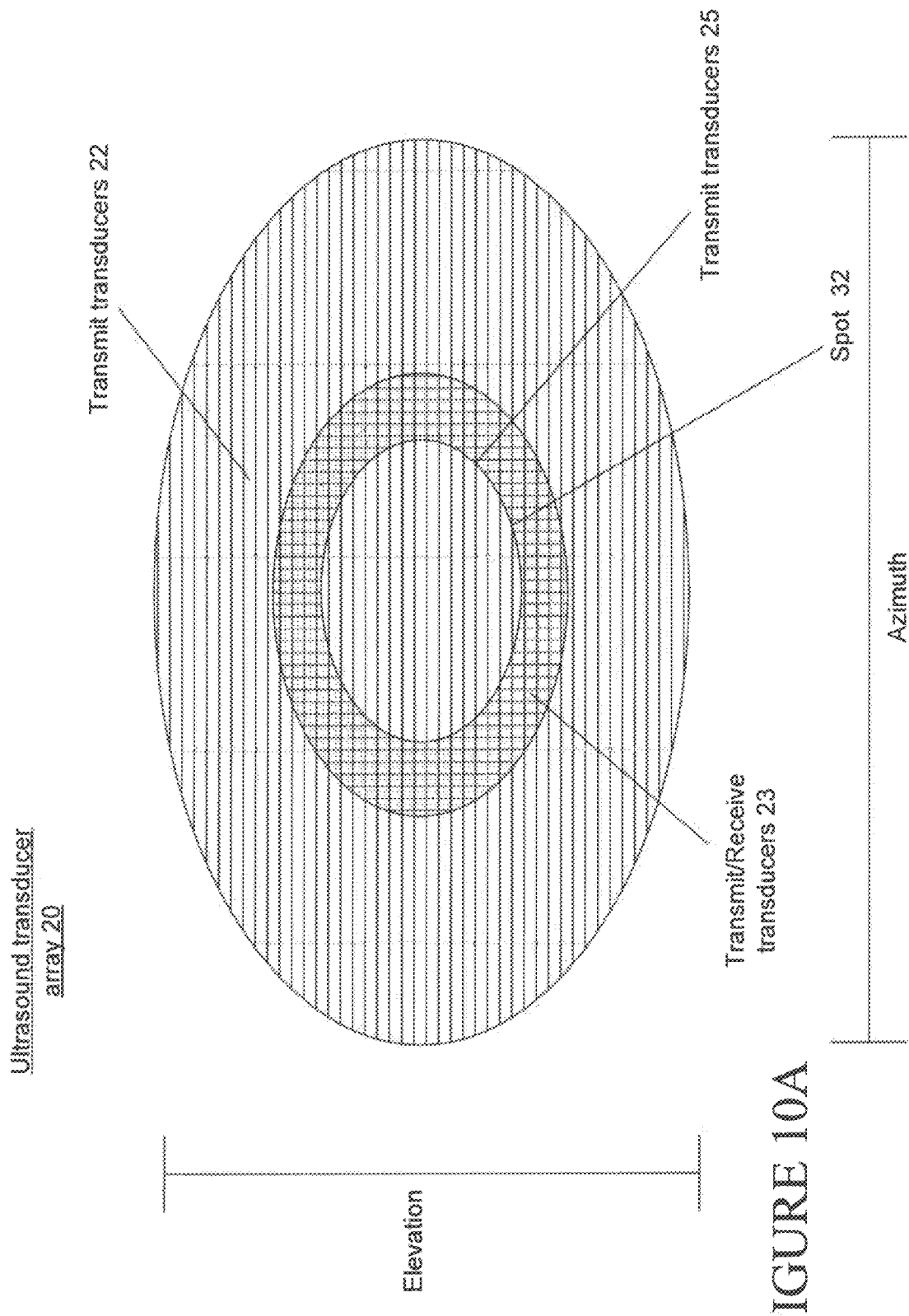
FIG. 10A illustrates an ultrasound transducer array according to an embodiment of the present invention having an elliptical aperture and an elliptical spot and having a transmit only area, a transmit/receive area and a transmit only spot area.

FIG. 10A illustrates an ultrasound transducer array 20 having an elliptical spot 32 and that includes transmit-only elements 22, transmit/receive elements 23 and transmit-only elements 25 in the spot area 32. The transmit-only elements 22 are transducers that exclusively transmit the ultrasonic waves. The transmit-only elements 25 in the spot 32 also exclusively transmit the ultrasonic waves and the transmit/receive elements 23 are transducer elements that can both transmit and receive the ultrasonic waves and can be switched such that the transmit/receive elements 23 can perform the function of a transmit element or the function of a receive element.

Embodiment 14

Circular Spot

Figure 9B:
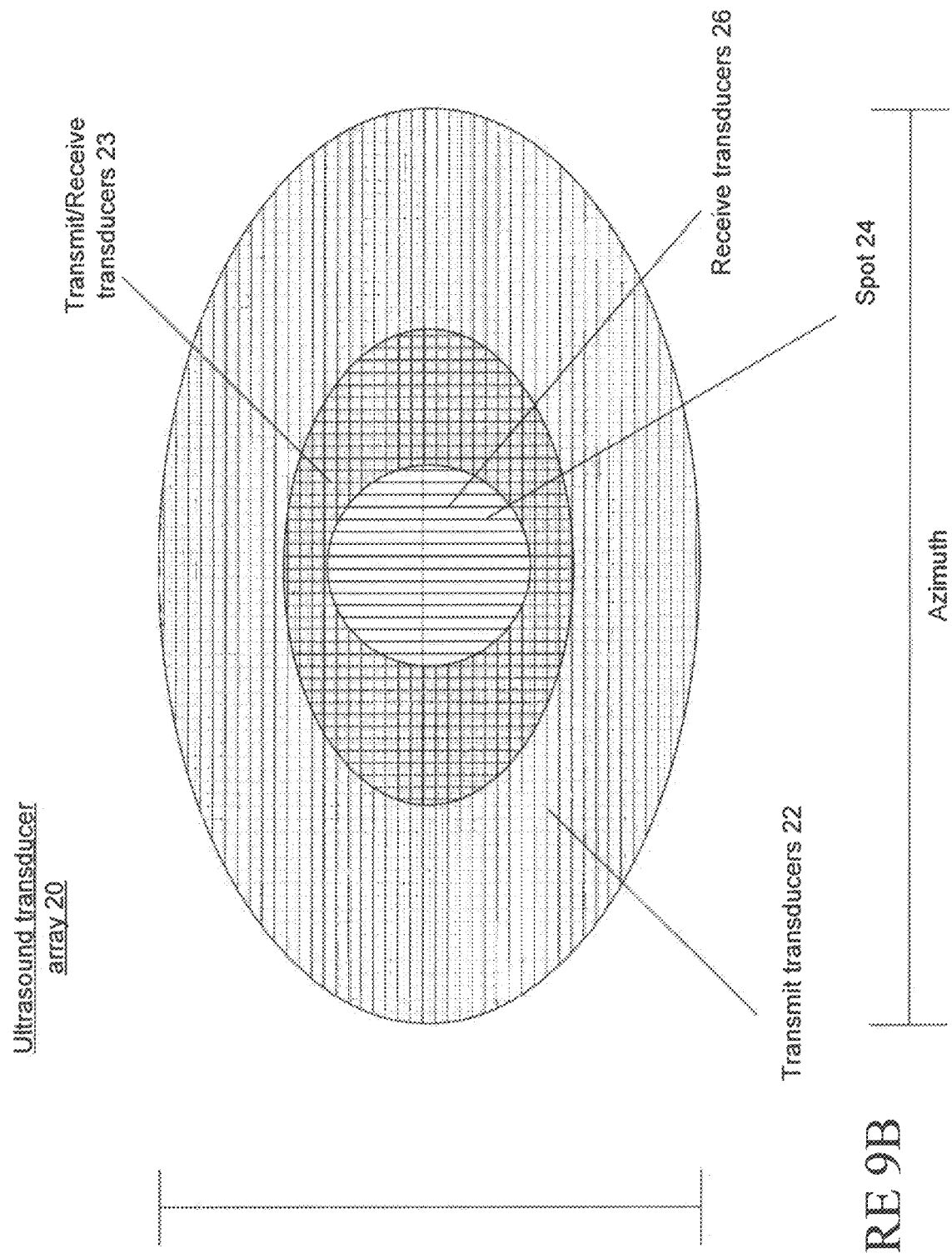
FIG. 9B illustrates an ultrasound transducer array according to an embodiment of the present invention having an elliptical aperture and a circular spot and having a transmit only area, a transmit/receive area and a receive only spot area.

FIG. 9B illustrates an ultrasound transducer array 20 having a circular spot 24 and that includes transmit-only elements 22, transmit/receive elements 23 and receive-only elements 26 in the spot area 24. The transmit-only elements 22 are transducers that exclusively transmit the ultrasonic waves. The receive-only elements 26 in the spot 24 exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 10B:
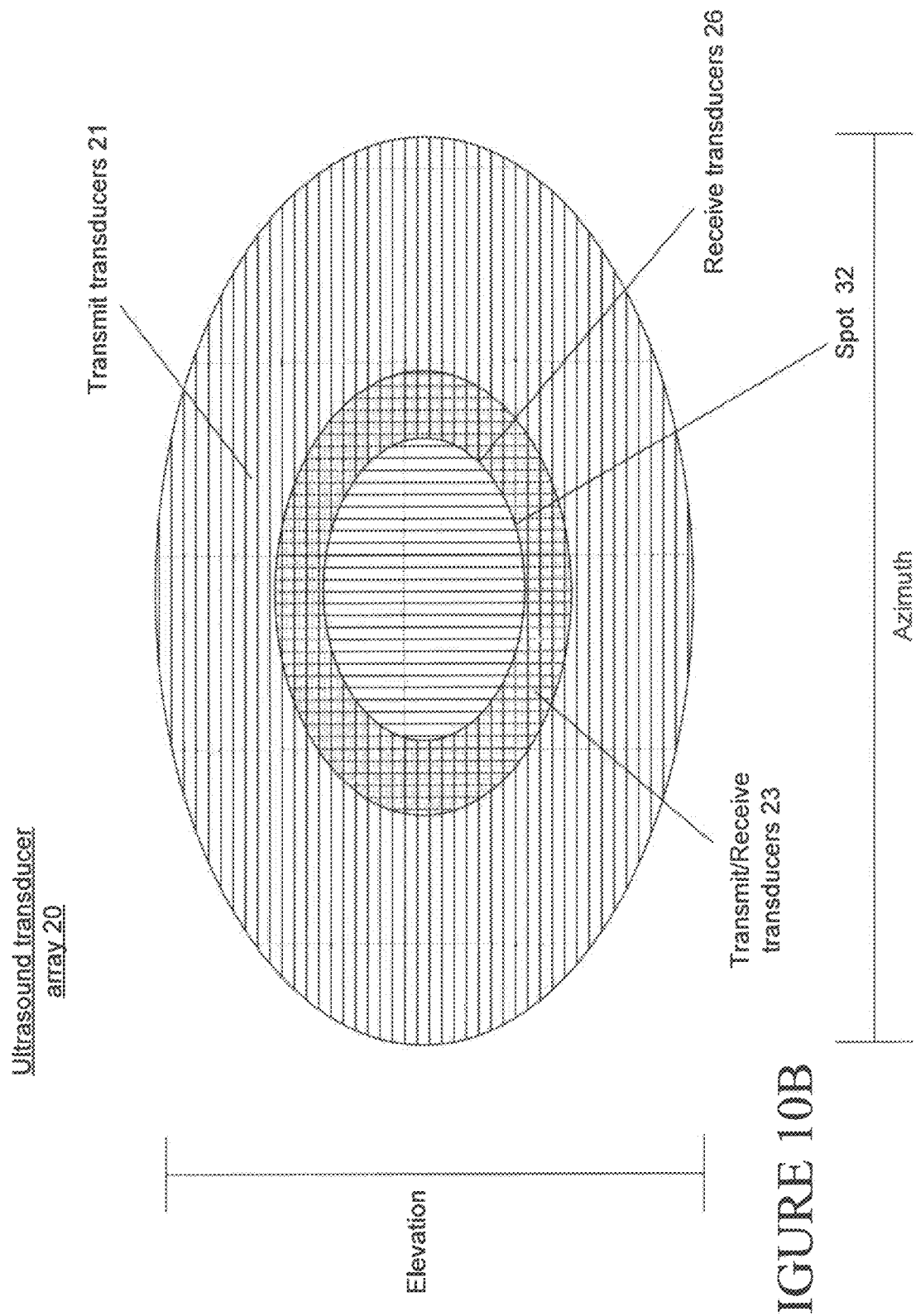
FIG. 10B illustrates an ultrasound transducer array according to an embodiment of the present invention having an elliptical aperture and an elliptical spot and having a transmit only area, a transmit/receive area and a receive only spot area.

FIG. 10B illustrates an ultrasound transducer array 20 having an elliptical spot 32 that includes transmit-only elements 21, transmit/receive elements 23 and receive-only elements 26 in the spot area 32. The transmit-only elements 21 are transducers that exclusively transmit the ultrasonic waves. The receive-only elements 26 in the spot 32 exclusively receive reflected ultrasound reverberations and the transmit/receive elements 23 are transducer elements that can both transmit and receive the ultrasonic waves and can be switched such that the transmit/receive elements 23 can perform the function of a transmit element or the function of a receive element.

Embodiment 15

Circular Spot

Figure 9C:
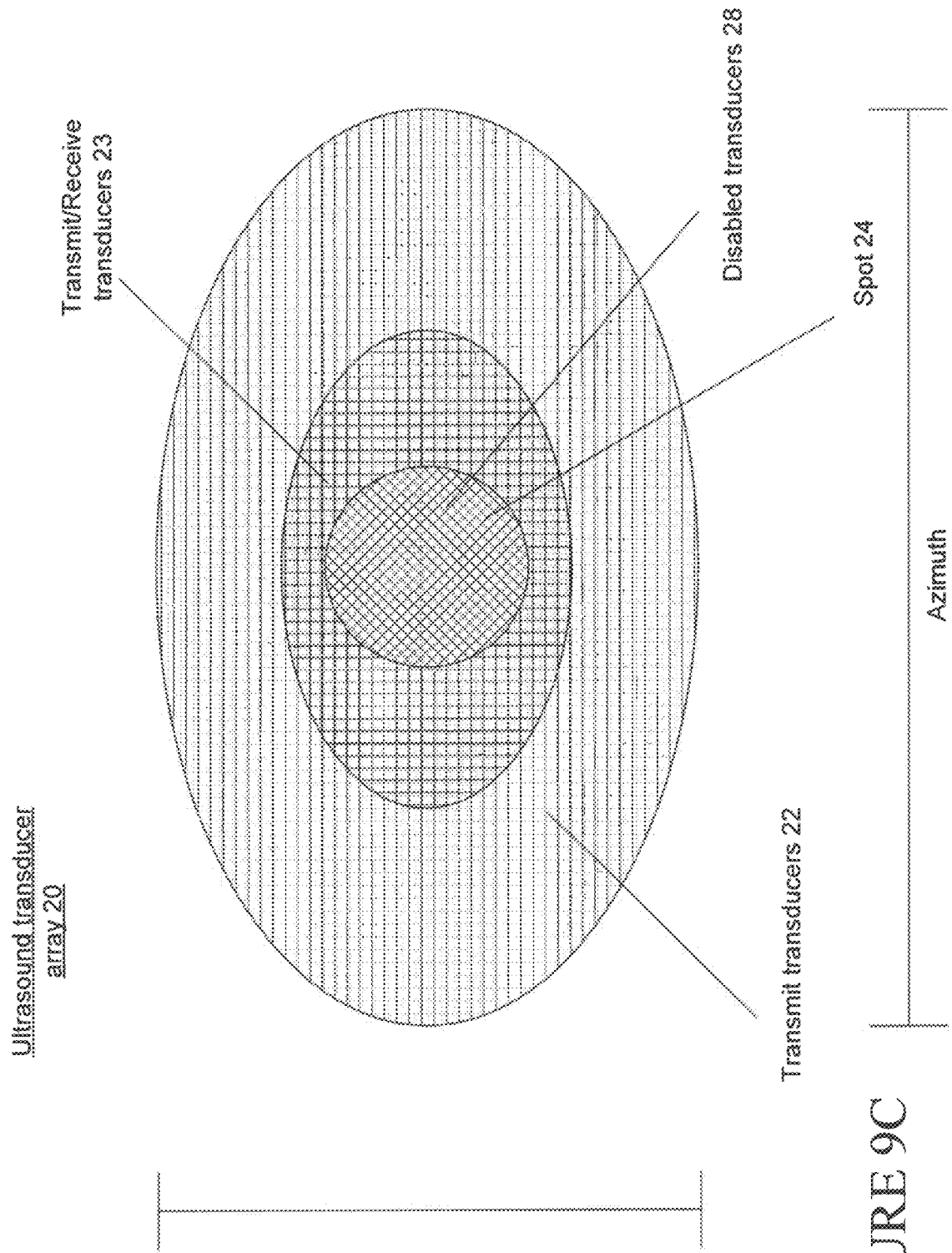
FIG. 9C illustrates an ultrasound transducer array according to an embodiment of the present invention having an elliptical aperture and a circular spot and having a transmit only area, a transmit/receive area and a disabled spot area.

FIG. 9C illustrates an ultrasound transducer array 20 having a circular spot 24 and that includes transmit-only elements 22, transmit/receive elements 23 and disabled elements 28 in the spot area 24. The transmit-only elements 22 are transducers that exclusively transmit the ultrasonic waves. The disabled elements 28 in the spot 24 are unable to transmit or to receive and the transmit/receive elements 23 are transducer elements that can both transmit and receive the ultrasonic waves and can be switched such that the transmit/receive elements 23 can perform the function of a transmit element or the function of a receive element.

(Elliptical Spot)

Figure 10C:
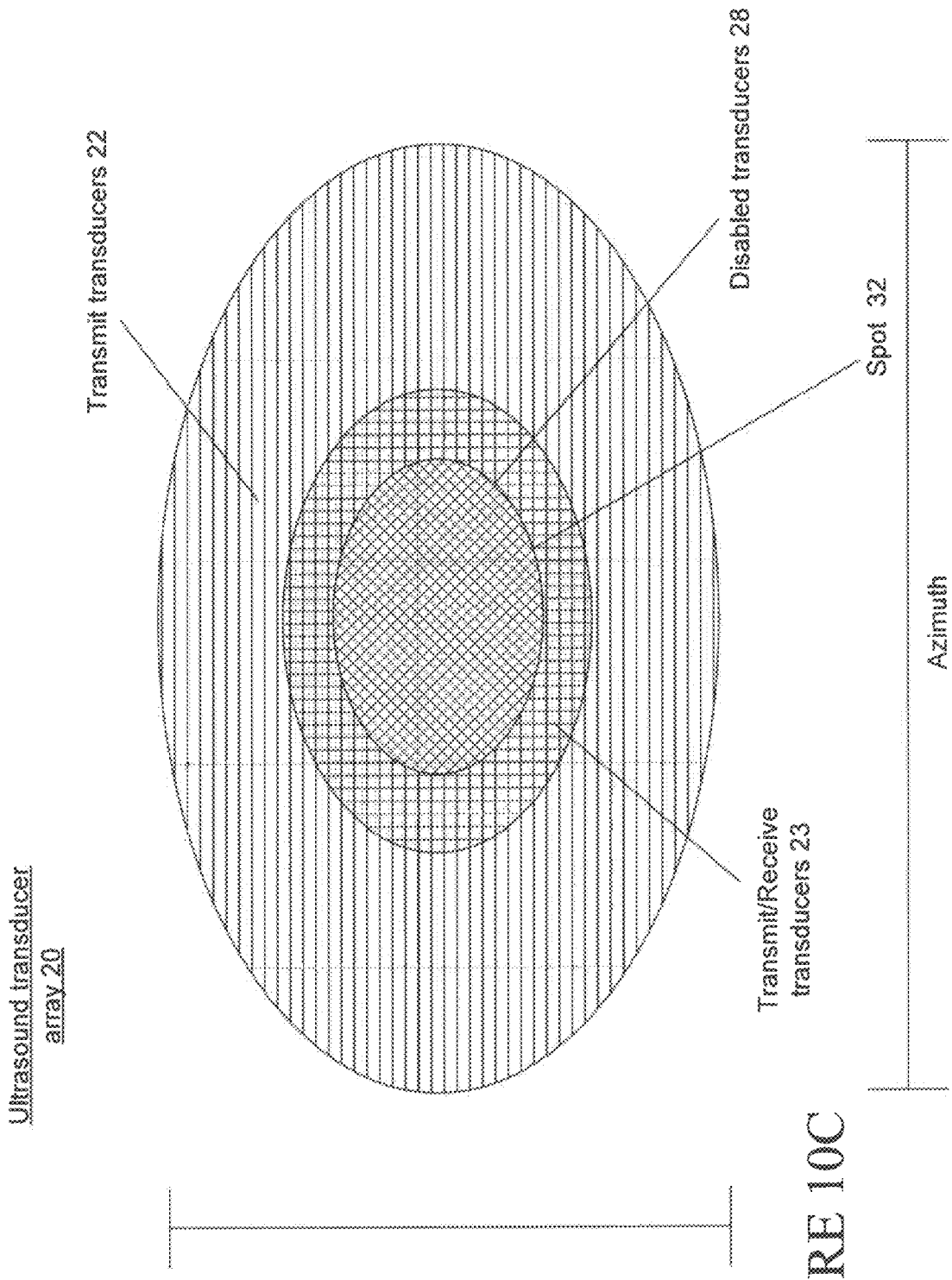
FIG. 10C illustrates an ultrasound transducer array according to an embodiment of the present invention having an elliptical aperture and an elliptical spot and having a transmit only area, a transmit/receive area and a disabled spot area.

FIG. 10C illustrates an ultrasound transducer array 20 having an elliptical spot 32 and that includes transmit-only elements 22, transmit/receive elements 23 and disabled elements 28 in the spot area 32. The transmit-only elements 22 are transducers that exclusively transmit the ultrasonic waves. The disabled elements 28 in the spot 32 are unable to transmit or to receive and the transmit/receive elements 23 are transducer elements that can both transmit and receive the ultrasonic waves and can be switched such that the transmit/receive elements 23 can perform the function of a transmit element or the function of a receive element.

Embodiment 16

Figure 11A:
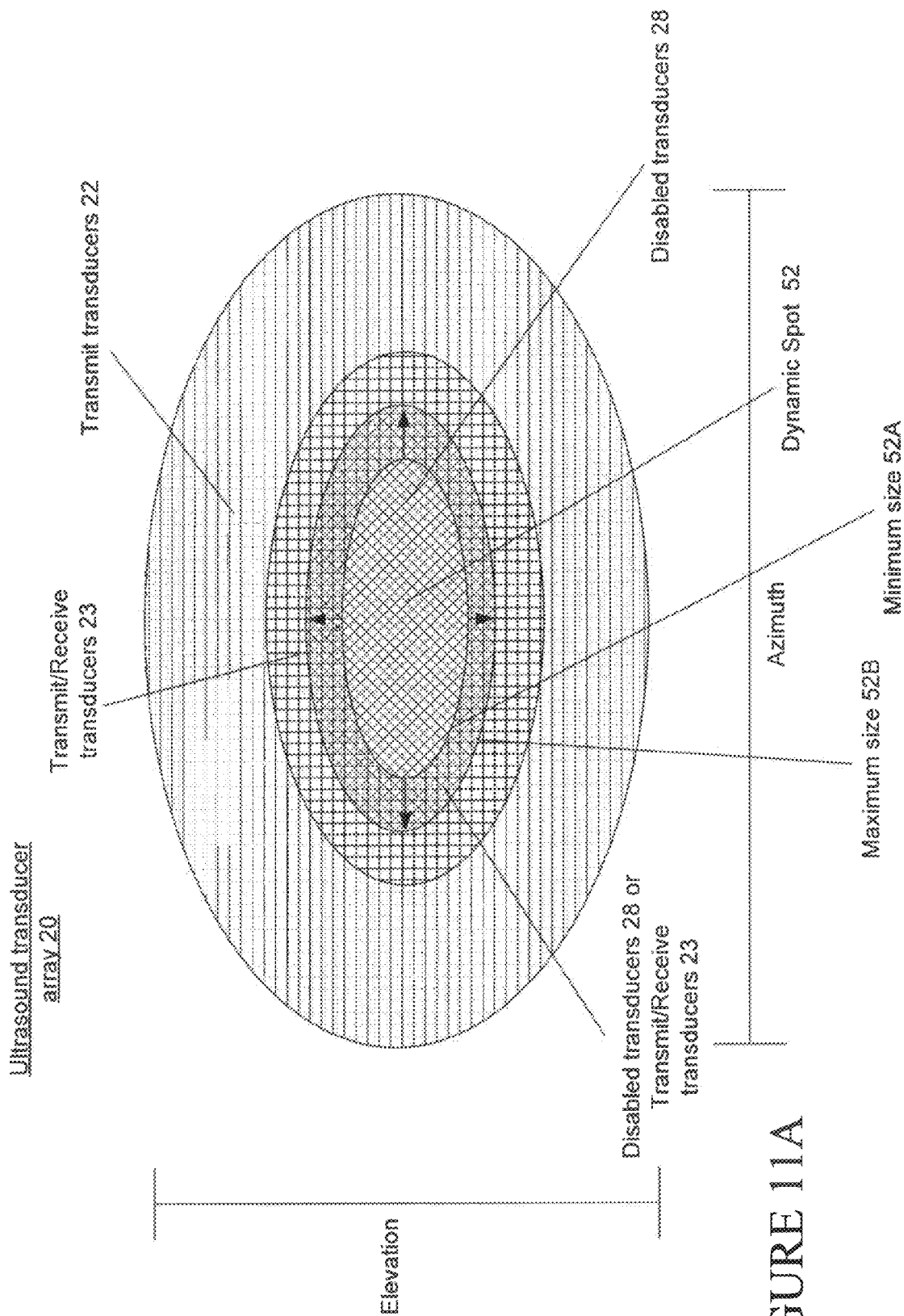
FIG. 11A illustrates an ultrasound transducer array according to an embodiment of the present invention having an elliptical aperture and a dynamic spot and having a transmit only area, a transmit/receive area, a disabled spot area, and a fourth area between the disabled spot area and the transmit/receive area which is switchable between being disabled and transmit/receive.

FIG. 11A illustrates an ultrasound transducer array 20 having a dynamic spot 52 and that includes transmit-only elements 22, transmit/receive elements 23 and disabled elements 28. The transmit-only elements 22 are transducers that exclusively transmit the ultrasonic waves. The disabled elements 28 in the spot 32 are unable to transmit or to receive and the transmit/receive elements 23 are transducer elements that can both transmit and receive the ultrasonic waves and can be switched such that the transmit/receive elements 23 can perform the function of a transmit element or the function of a receive element.

Figure 11B:
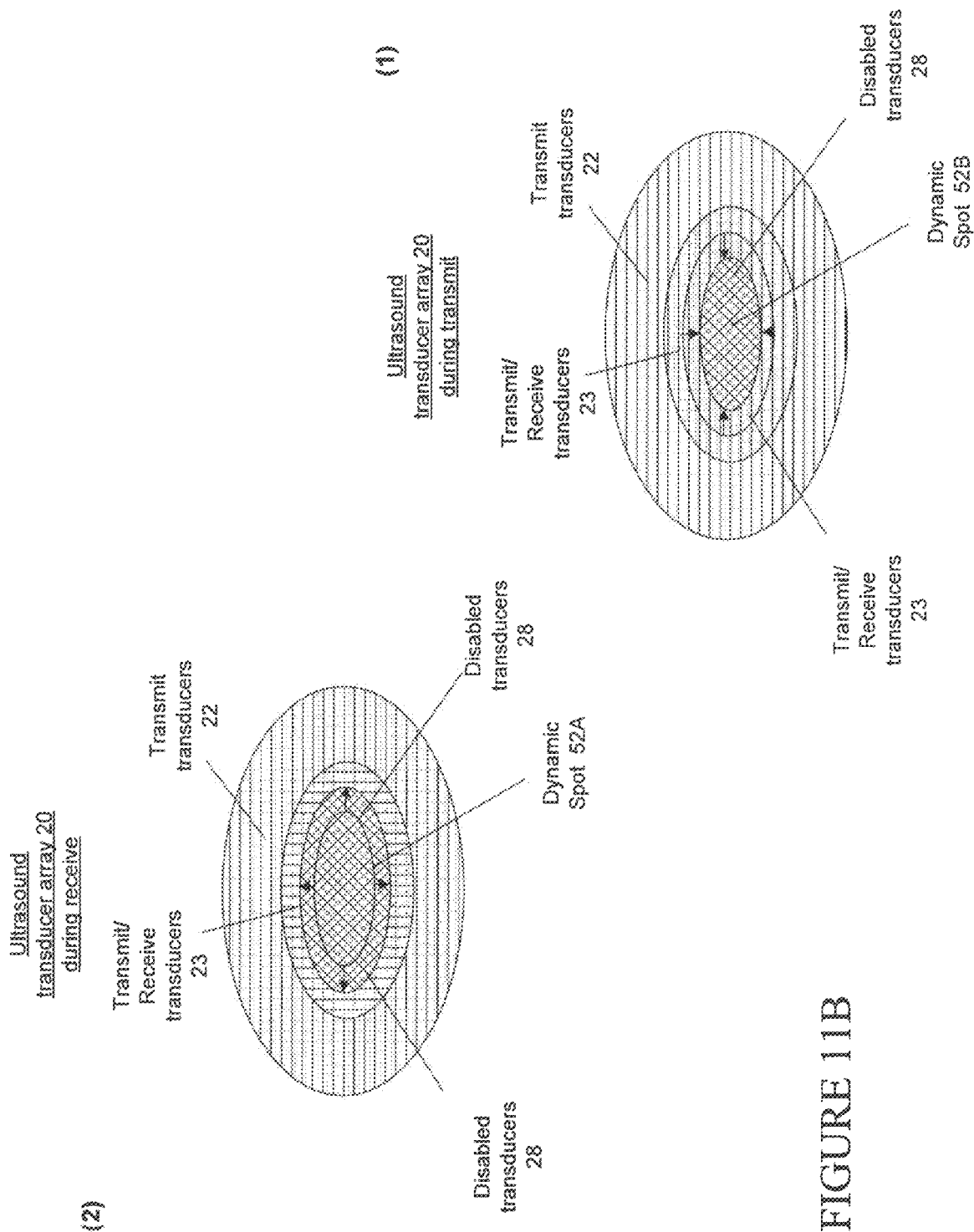
FIG. 11B illustrates an ultrasound transducer array according to an embodiment of the present invention having different dynamic spot sizes during receive and during transmit, the ultrasound transducer array having an elliptical aperture and a dynamic spot having a transmit only area, a transmit/receive area, a disabled spot area, and a fourth area between the disabled spot area and the transmit/receive area which is switchable between being disabled and transmit/receive.

FIG. 11B illustrates an ultrasound transducer array according to an embodiment of the present invention having different dynamic spot sizes during receive and during transmit. The transducer arrays shown in FIG. 11B have the structure as the transducer array in FIG. 11A. However, in the example shown in FIG. 11B, when the transducer array 20 is transmitting the ultrasound signal as is shown in FIG. 11B-(1), the transmit transducers 22 are transmitting, the receive/transmit transducers 23 are set to transmit and are performing a transmit function, the transducers in the switchable area 55B are set to transmit, and the transducers in the spot area 28 are disabled. The dynamic spot 52 thus has a first size during transmit which corresponds to the size of the disabled spot area 28. In contrast, in FIG. 11B-(2) there is shown an example corresponding to when the transducer array is in receive mode. In the example of receive mode, the transmit-only transducers 22 are inactive, the receive/transmit transducers 23 are set to receive and are performing a receive function, the transducers in the switchable area 55 are set to disabled, and the transducers in the spot area 28 are disabled. Thus, the dynamic spot 52A has a second size during receive which corresponds to a combination of the size of the disabled spot area 28 and the switchable area 55. This example can also function when the spot area is transmit-only, receive-only and transmit/receive. Thus, as is shown in FIG. 3C, the dynamic spot 52 has different sizes during transmit and receive.

Embodiment 17

The ultrasound transducer array having the structure shown in FIG. 11A (dynamic spot 52 and that includes transmit-only elements 22, transmit/receive elements 23 and disabled elements 28) can be used in the example shown in FIG. 4A. As is noted above, FIG. 4A illustrates graphs (1) and (2) showing the size of the dynamic spot over time when the size of the spot during transmit is different than the size of the spot during receive. In addition, FIG. 4A illustrates that during receive, the size of the dynamic spot 52A can change (is dynamic) during the reception of the ultrasonic beam. Thus, the dynamic spot 52A/B shown in FIG. 11A can have different sizes during transmit and receive and the size of the dynamic spot 52A can change during receive.

Embodiment 18

The ultrasound transducer array having the structure shown in FIG. 11A (dynamic spot 52 and that includes transmit-only elements 22, transmit/receive elements 23 and disabled elements 28) can be used in the example shown in FIG. 4B. FIG. 4B illustrates a graph showing the size of the dynamic spot over time when the size of the spot during transmit is different than the size of the spot during receive. In addition, FIG. 4B illustrates that during receive the size of the dynamic spot 52 can change during the reception of the ultrasonic beam. Moreover, FIG. 4B illustrates that the size of the dynamic spot 52 can change from beam to beam. Thus, the dynamic spot 52 shown in FIG. 11A can have different sizes during transmit and receive, the size of the dynamic spot 52 can change during receive, and the size of the dynamic spot 52 can change from beam to beam.

Figure 12:
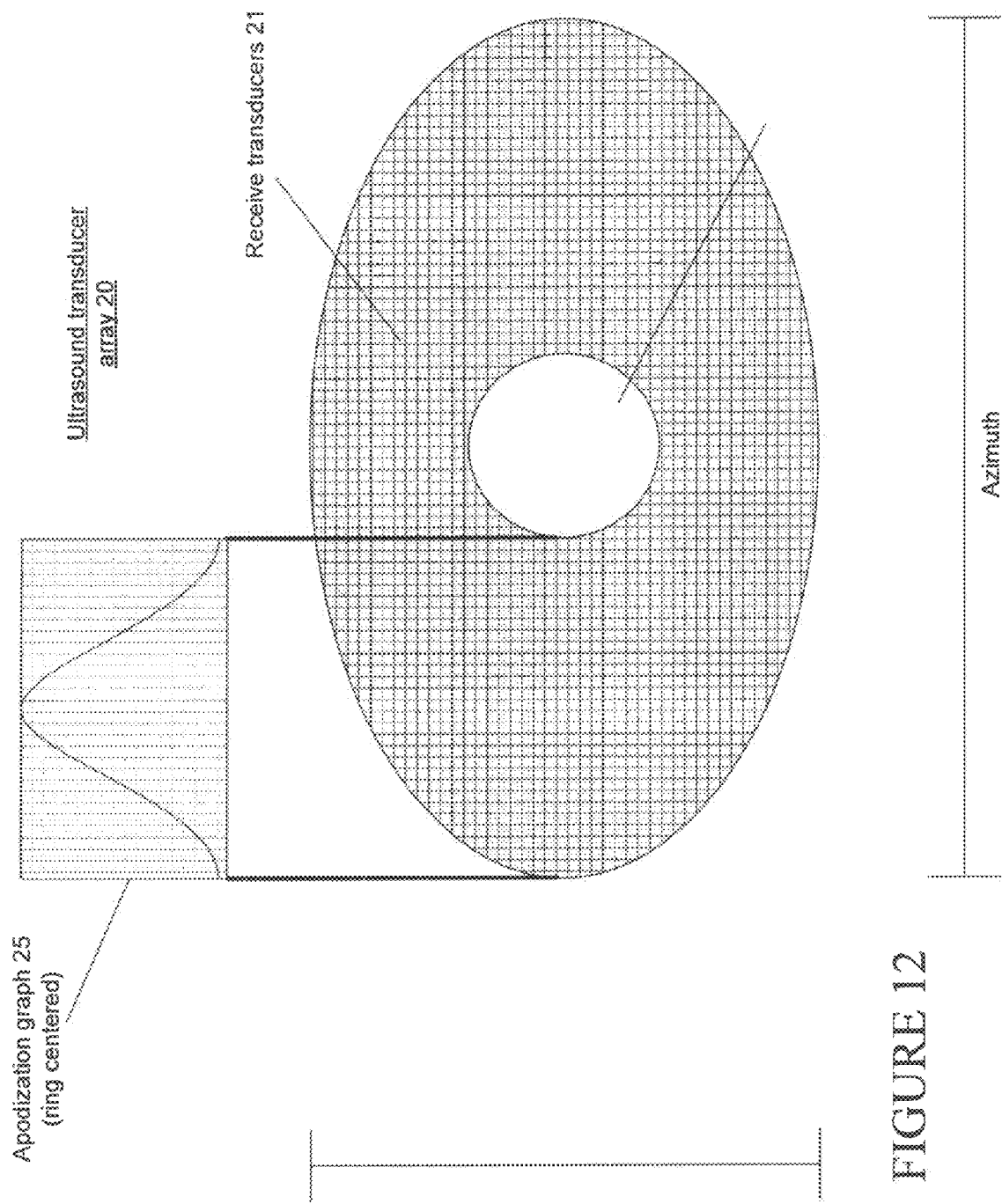
FIG. 12 illustrates an ultrasound transducer array according to an embodiment of the present invention for which a ring centered apodization graph is provided.
Figure 13:
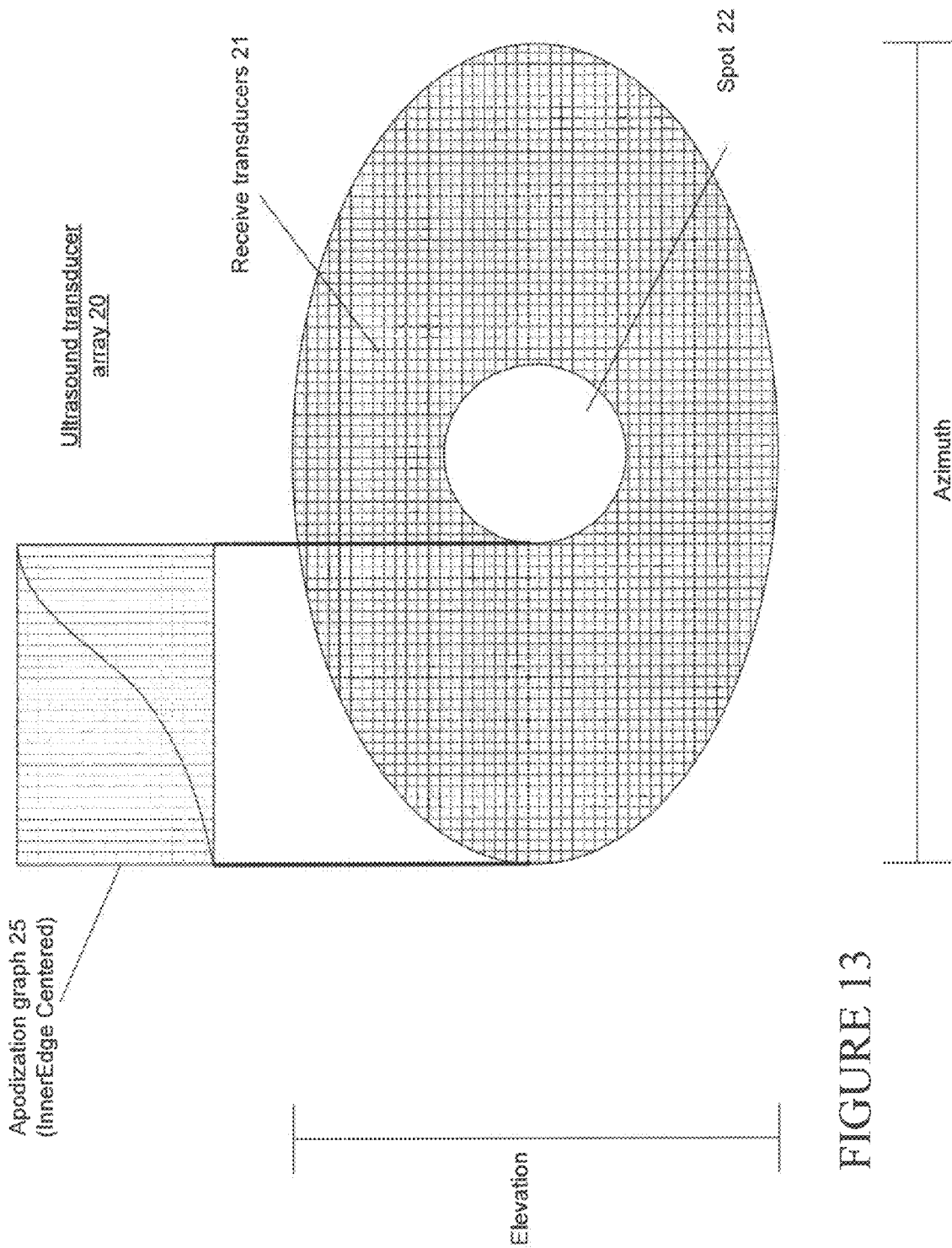
FIG. 13 illustrates an ultrasound transducer array according to an embodiment of the present invention for which an inner-edge centered apodization graph is provided.

FIGS. 12 and 13 relate to apodization. Apodization is generally applied in both 1-d and 2-d arrays so that the maximum signal is generated at the center of the array and the minimum signal, as defined by hamming/hanning/raised cosine/etc. apodization weighting, is applied at the elements farthest away from the active aperture center.

Standard Fresnel Lens Theory suggests that a sine-weighted apodization profile across each of the Fresnel rings will focus energy more finely at the designated focal point. In one embodiment, ring-centered apodization, similar to the optics theory mentioned above, and shown in the apodization graph 25 of FIG. 12, is utilized in order to result in a similar imaging focus improvement. In addition, ring-centered apodization is used at one location in the image (the near and mid-field, for example) and inner-edge centered apodization (shown in FIG. 13) is used in the mid-to-far field for highest sensitivity, and apodization flattening in the very far field. See apodization graph 25 of FIG. 12 which illustrates that the apodization is centered on the edge of the spot 22 and not in the middle of the aperture as is typical. Thus, whereas the ring-centered apodization is helpful in a number of instances, an apodization profile that changes for optimization of parameters other than focusing parameters may also be called for when optimizing an ultrasound image.

Different types of apodization can be used for an ultrasound system. Specifically, one type, transmit apodization, is performed by weighting the energy of the transmitting waveform. This can be accomplished by changing the amplitude of each of the waveforms across the transducer element array, or by changing the amount of energy available in the pulse though the use of pulse width modulation, for example. Transmit apodization can provide improvements in imaging performance. A second type, receive apodization, is applied by multiplying the incoming signal with a "weight" for that channel. For analog systems, this is accomplished through gain control associated with each channel, for digital systems that use analog to digital conversion before apodization processing, apodization is accomplished by multiplying the digital signal by a digital apodization weighting term within the beamformer.

In addition, apodization weighting can be applied to summed sub-array elements. When using sub-array elements, the summed receive signals from n elements, either directly summed, or summed after relative delay, are applied to each of the channels, before apodization is applied.

Figure 14:
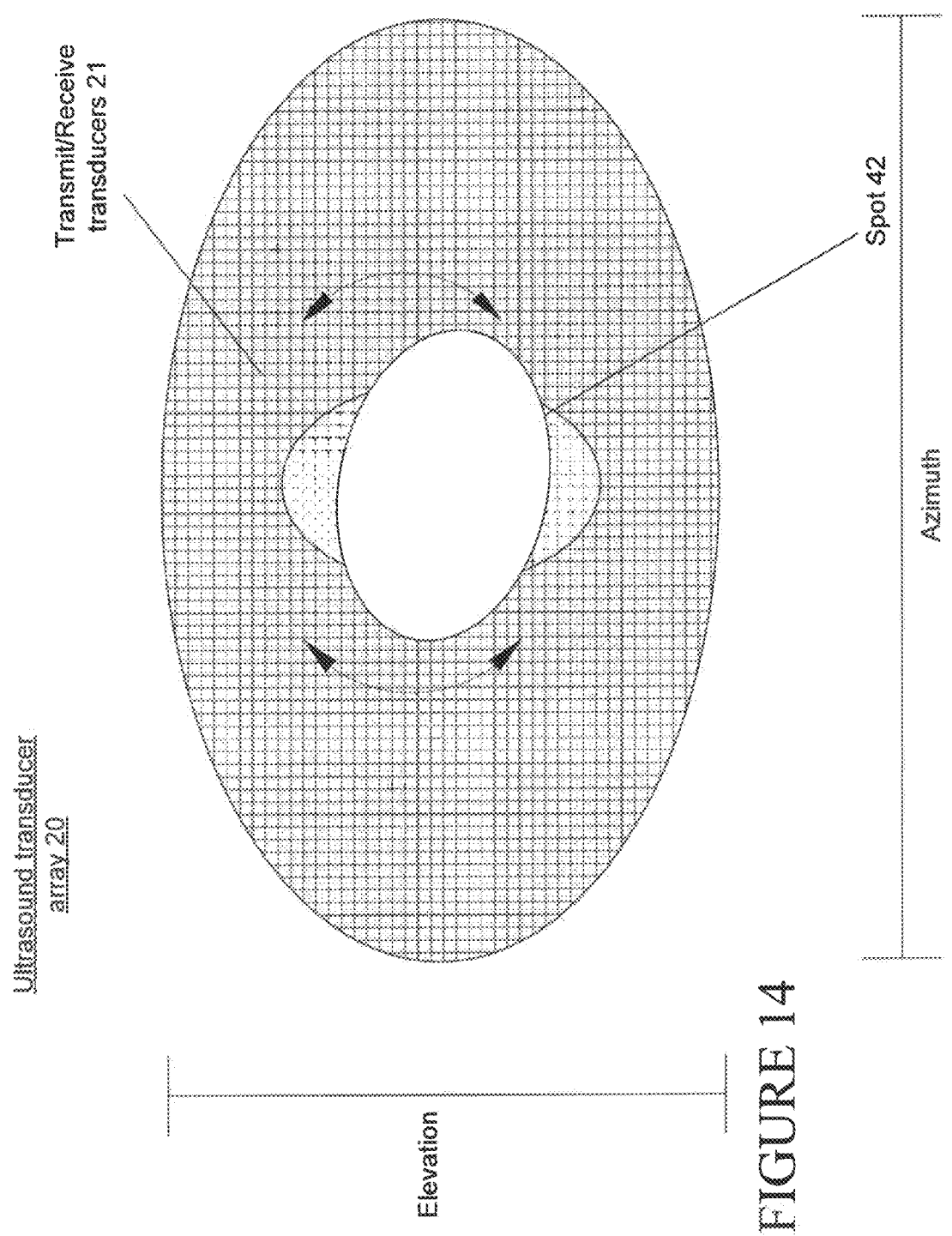
FIG. 14 illustrates an ultrasound transducer array according to an embodiment of the present invention in which illustrates that the spot can be rotated in any combination of azimuth/elevation direction.

FIG. 14 illustrates that the spot 42 can be arranged in any combination of the elevation/azimuth direction. Although the examples of the transducer array noted above illustrate the spot in one configuration, as is shown in FIG. 14, the spot whether it be a circle, an ellipse or some other shape, can be arranged in any direction. In addition, the spot can be arranged off-centered as well as centered on the array. In addition, the spot 42 can be used when steering beams for both transmit and receive apertures. Further, the spot can be arranged such that it may be optimally used with steered beams in the azimuth direction, the elevation direction or in an elevation/azimuth direction.

In addition, for receive apertures, dynamic change of the spot 52 can occur on a depth basis, as well. For instance, the spot 52 can be dynamically updated with receive depth, in a similar way that present ultrasound systems perform aperture growth—including more channels, and increasing the receive aperture size, as the receive focusing depth is dynamically updated.

Figure 15:
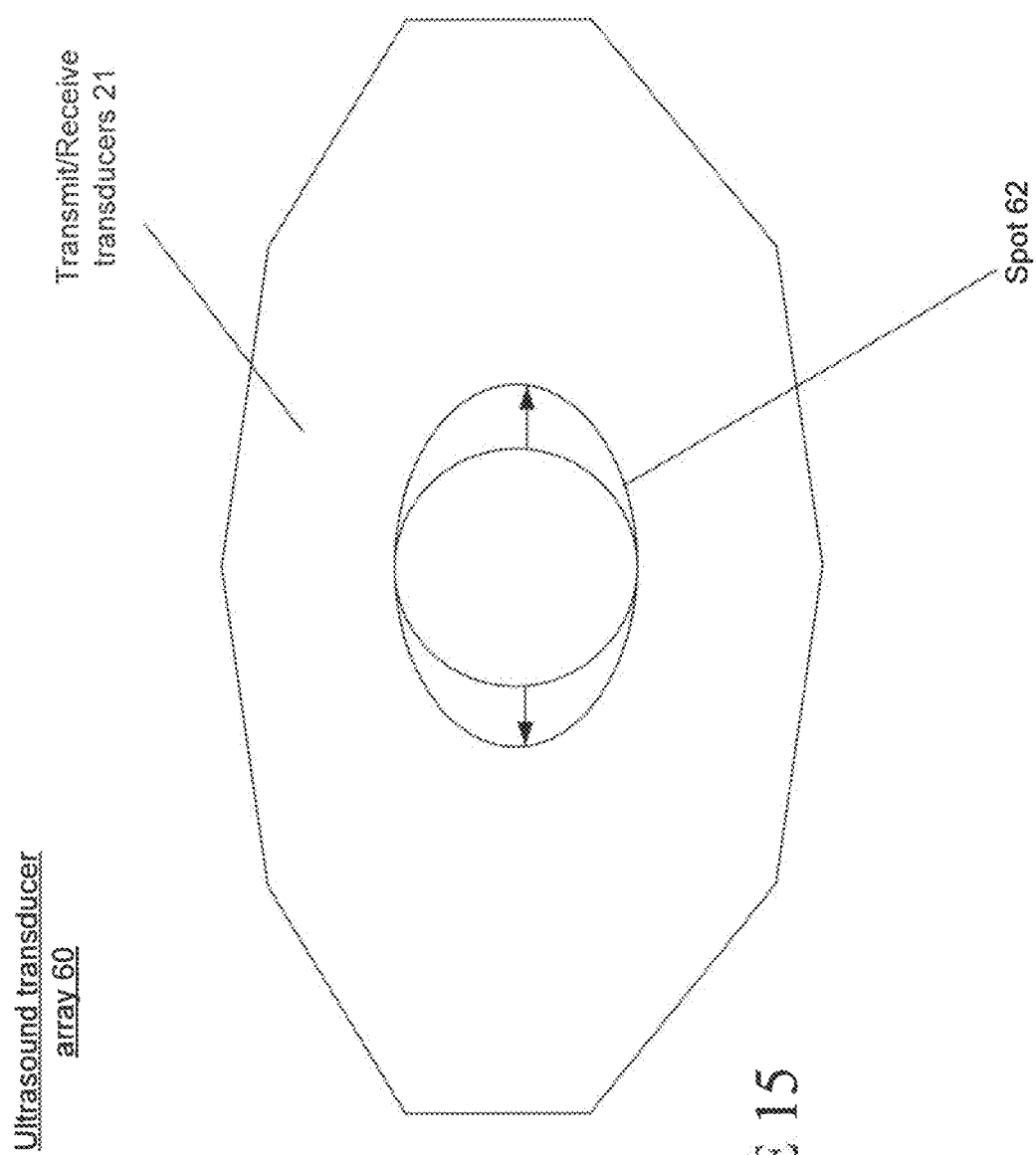
FIG. 15 illustrates an ultrasound transducer array according to an embodiment of the present invention having a polygonal aperture.

The embodiments noted above where described as having elliptical arrays, however, the present invention can also be implemented using a polygonal array. The polygonal array shown in FIG. 15 includes an array of transducer elements 60 which include transmit/receive 21 elements and a spot 62. The polygonal array can be used with any of the embodiments noted above.

Figure 16:
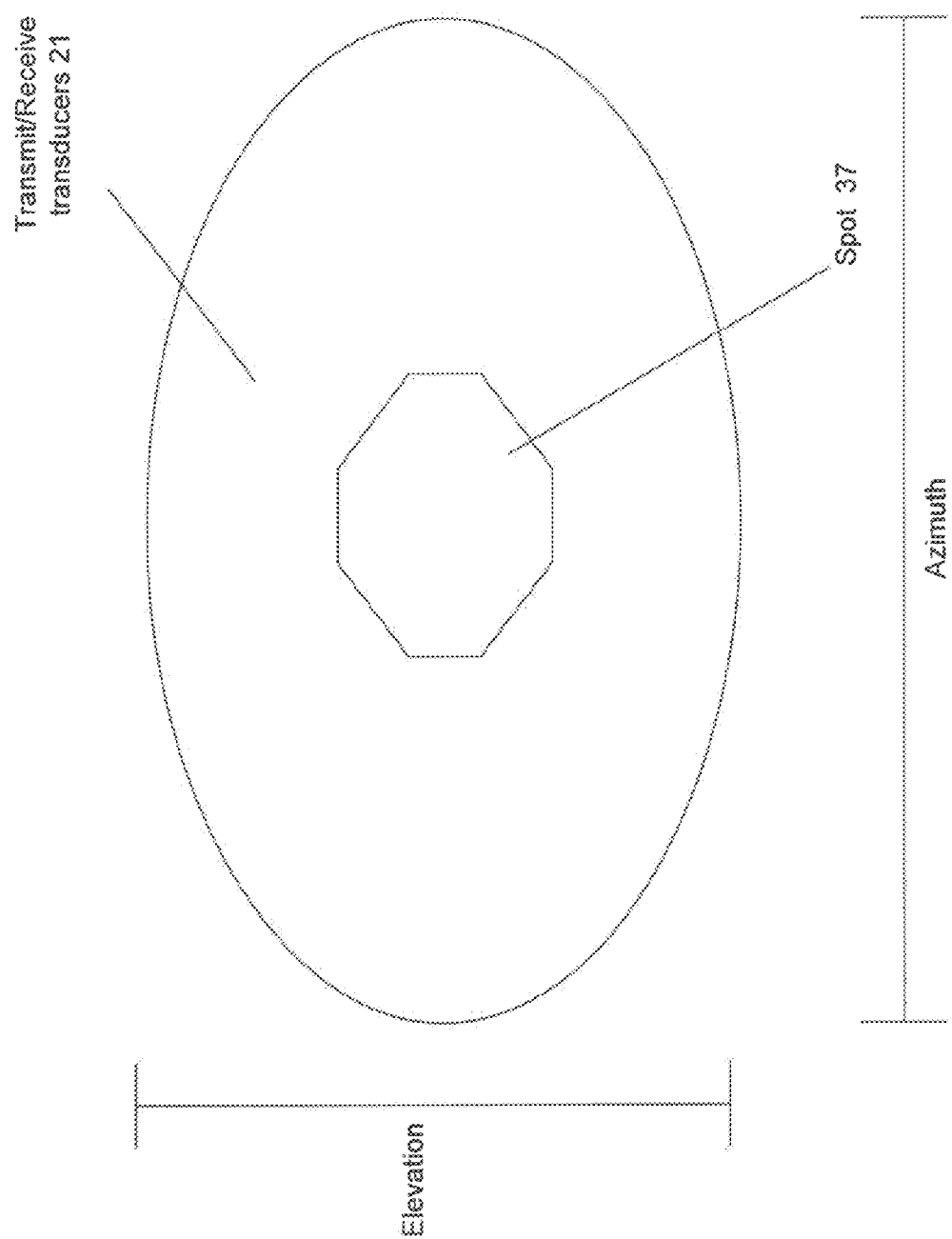
FIG. 16 illustrates an ultrasound transducer array according to an embodiment of the present invention having an elliptical aperture and a polygonal spot.

In addition the shape of the spot or the shape that the dynamic spot creates could be a polygonal shape 37. This shape could be, for example, an irregular polygon. FIG. 16 illustrates an example of a spot which has a polygonal shape.

Figure 17:
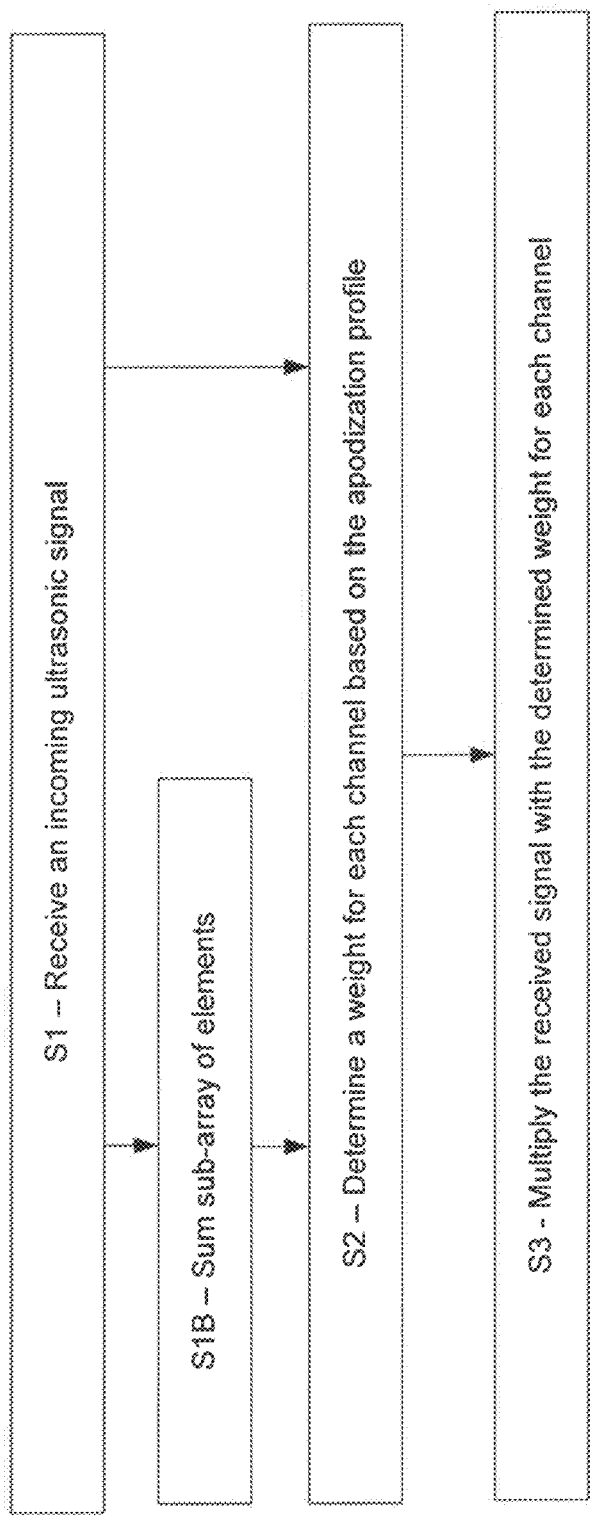
FIG. 17 illustrates a flow diagram illustrating a method according to an embodiment of the present invention.

FIG. 17 shows a flow diagram indicating the process steps performed by the apodization in one embodiment of the present invention. In step S1, the incoming ultrasonic signal is received. The flow can either follow one of two paths. First if the summation of sub-arrays is not applied, the flow proceeds to step S2. However, if the summation of sub-arrays is applied, the summed receive signals from n elements, either directly summed, or summed after relative delay, are applied to each of the channels S1B before proceeding to step S2. In step S2, a weight for each incoming channel is determined based on an apodization profile (such as ring-centered or inner-edge centered). Once the weight for each channel has been determined, in step S3, the received signal for each channel is multiplied by the weight determined in step S2. As is noted above, this process can be performed using analog or digital signals and can be performed using both analog circuits or a digital computer based system.

Figure 18:
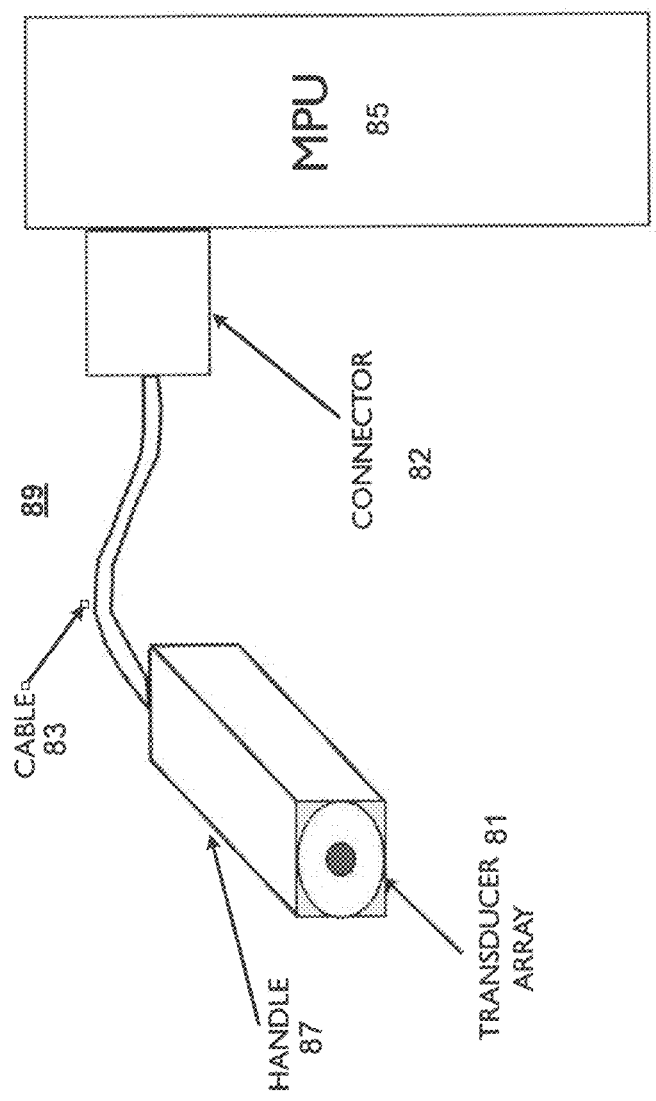
FIG. 18 illustrates an ultrasound device according to an embodiment of the present invention having a main processing unit, a connector, a cable, a handle and a transducer array.

FIG. 18 illustrates an exemplary ultrasound imaging device 89. Included in the ultrasound imaging device 89 are a main processing unit 85. This device could be connected to several input/output devices. Also connected to the main processing unit 85 is a connector 82 and a cable 83 which is connected to transducer array 81 via a handle 87. The head of the handle 87 includes an array of elements 81 which can include a spot area as is described above. Processing necessary for performance of the ultrasonographic imaging process may be performed entirely or partly by the main processing unit 85 or alternatively partly or entirely in the probe—82, 83, 87 and 81. For example, the processing necessary to enable and disable elements in the spot area of the dynamic spot 52 can be performed by the main processing unit 85 (or within the probe, itself).

Figure 19A:
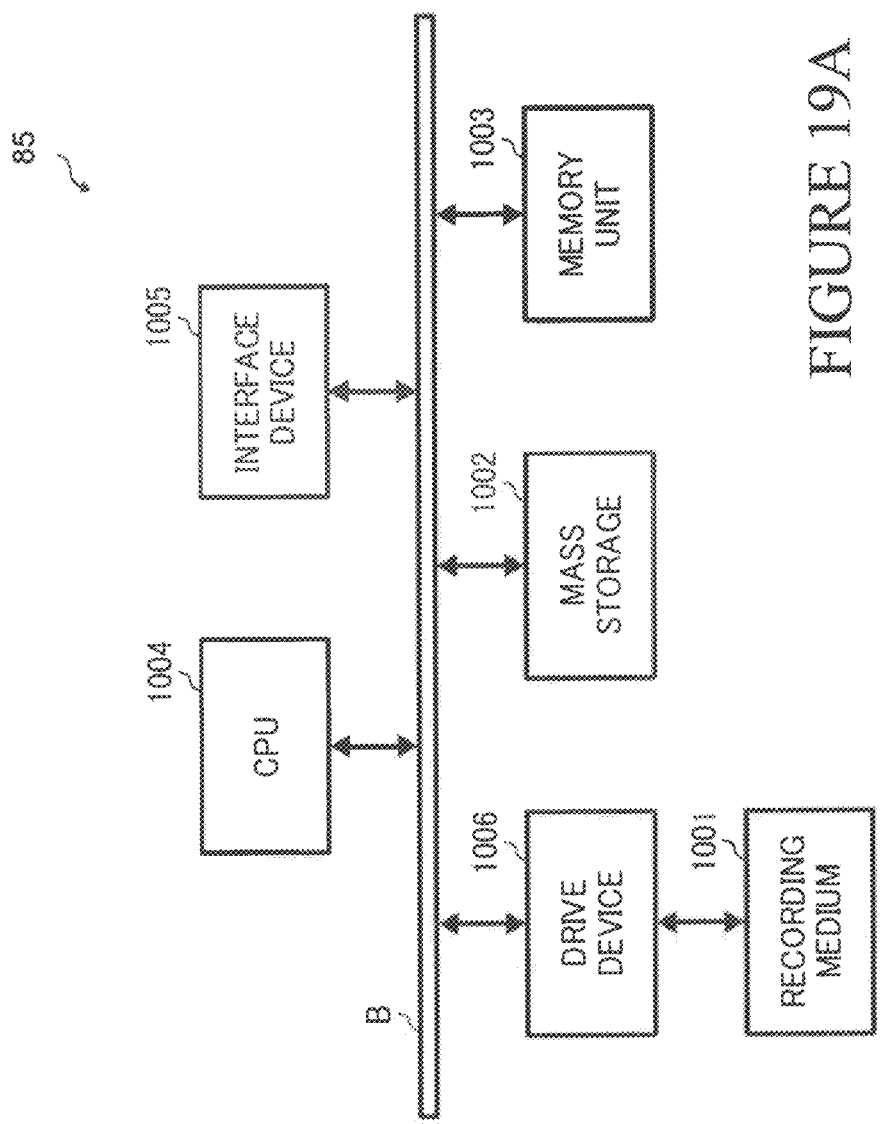
FIG. 19A illustrates an exemplary structure of the main processing unit according to an embodiment of the present invention.
Figure 19B:
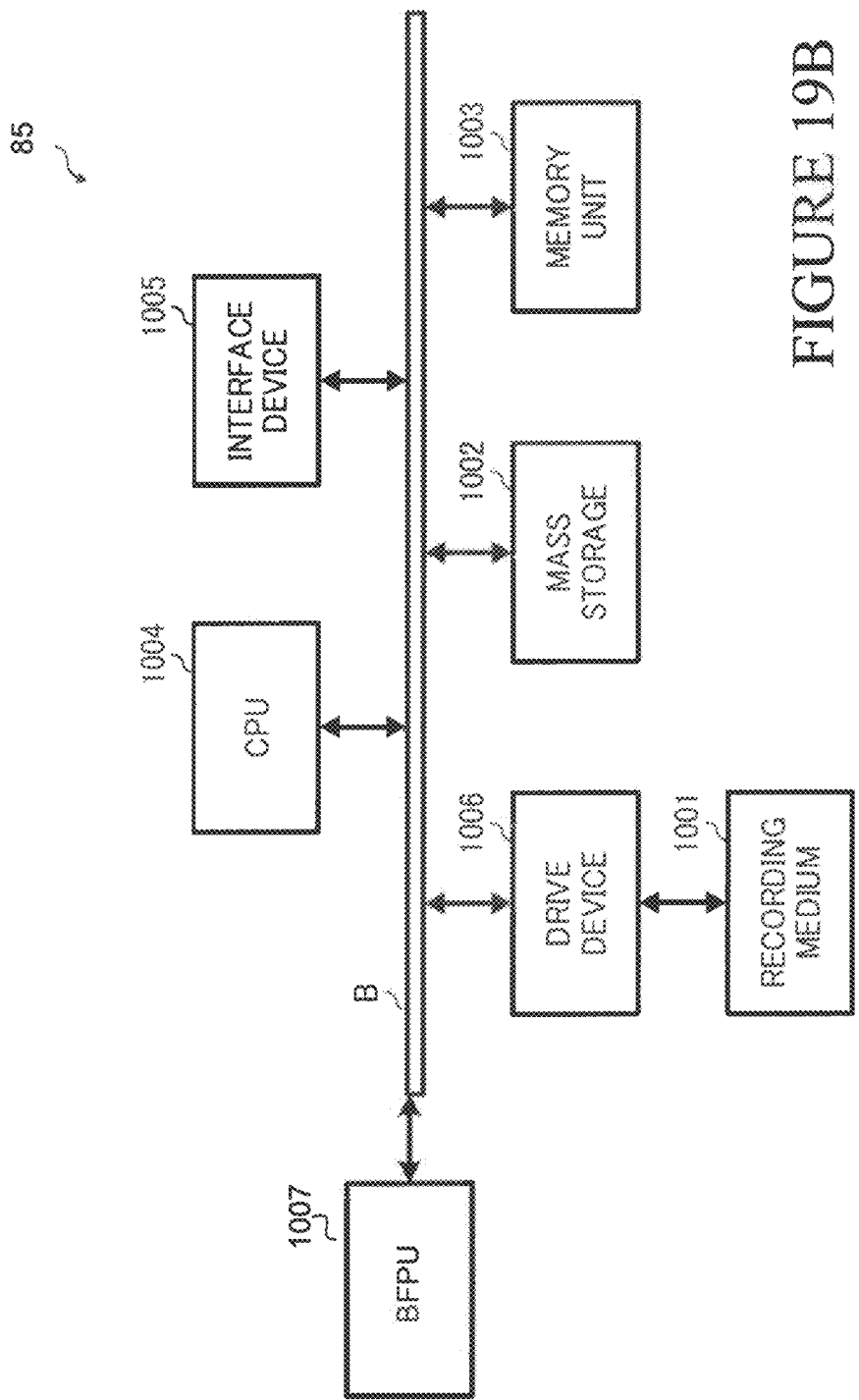
FIG. 19B illustrates an exemplary structure of the main processing unit according to an embodiment of the present invention.

FIGS. 19A and 19B illustrate the structure of, for example, the main processing unit 85 according to an embodiment of the invention. The MPU 85 shown in FIGS. 19A and 19B are identical except for the inclusion in the MPU 85 in 19B of a beamformer processing unit (BFPU) 1007. In the embodiment shown in FIG. 19A, the BFPU is not located in the MPU 85 but is instead located in an alternate location such as in the probe.

The main processing unit 85 includes a bus B or other communication mechanism for communicating information, and a processor/CPU 1004 coupled with the bus B for processing the information. The main processing unit 85 also includes a main memory/memory unit 1003, such as a random access memory (RAM) or other dynamic storage device (e.g., dynamic RAM (DRAM), static RAM (SRAM), and synchronous DRAM (SDRAM)), coupled to the bus B for storing information and instructions to be executed by processor/CPU 1004. In addition, the memory unit 1003 may be used for storing temporary variables or other intermediate information during the execution of instructions by the CPU 1004. The main processing unit 85 may also further include a read only memory (ROM) or other static storage device (e.g., programmable ROM (PROM), erasable PROM (EPROM), and electrically erasable PROM (EEPROM)) coupled to the bus B for storing static information and instructions for the CPU 1004.

The main processing unit 85 may also include a disk controller coupled to the bus B to control one or more storage devices for storing information and instructions, such as mass storage 1002, and drive device 1006 (e.g., floppy disk drive, read-only compact disc drive, read/write compact disc drive, compact disc jukebox, tape drive, and removable magneto-optical drive). The storage devices may be added to the main processing unit 85 using an appropriate device interface (e.g., small computer system interface (SCSI), integrated device electronics (IDE), enhanced-IDE (E-IDE), direct memory access (DMA), or ultra-DMA).

The main processing unit 85 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The main processing unit 85 may also include a display controller coupled to the bus B to control a display, such as a cathode ray tube (CRT), for displaying information to a computer user. The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer may provide printed listings of data stored and/or generated by the computer system.

The main processing unit 85 performs at least a portion of the processing steps of the invention in response to the CPU 1004 executing one or more sequences of one or more instructions contained in a memory, such as the memory unit 1003. Such instructions may be read into the memory unit from another computer readable medium, such as the mass storage 1002 or a removable media 1001. One or more processors in a multi-processing arrangement may also be employed to execute the sequences of instructions contained in memory unit 1003. In alternative embodiments, hard-wired circuitry may be used in place of or in combination with software instructions. Thus, embodiments are not limited to any specific combination of hardware circuitry and software.

As stated above, the main processing unit 85 includes at least one computer readable medium 1001 or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read.

Stored on any one or on a combination of computer readable media, the present invention includes software for controlling the main processing unit 85, for driving a device or devices for implementing the invention, and for enabling the main processing unit 85 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code elements on the medium of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the CPU 1004 for execution. A computer readable medium may take many forms, including but not limited to, non-volatile media, and volatile media. Non-volatile media includes, for example, optical, magnetic disks, and magneto-optical disks, such as the mass storage 1002 or the removable media 1001. Volatile media includes dynamic memory, such as the memory unit 1003.

Various forms of computer readable media may be involved in carrying out one or more sequences of one or more instructions to the CPU 1004 for execution. For example, the instructions may initially be carried on a magnetic disk of a remote computer. An input coupled to the bus B can receive the data and place the data on the bus B. The bus B carries the data to the memory unit 1003, from which the CPU 1004 retrieves and executes the instructions. The instructions received by the memory unit 1003 may optionally be stored on mass storage 1002 either before or after execution by the CPU 1004.

The main processing unit 85 also includes a communication interface 1005 coupled to the bus B. The communication interface 1004 provides a two-way data communication coupling to a network that is connected to, for example, a local area network (LAN), or to another communications network such as the Internet. For example, the communication interface 1005 may be a network interface card to attach to any packet switched LAN. As another example, the communication interface 1005 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1005 sends and receives electrical, electromagnetic or optical signals that carry digital data streams representing various types of information.

The network typically provides data communication through one or more networks to other data devices. For example, the network may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). Moreover, the network may provide a connection to a mobile device such as a personal digital assistant (PDA) laptop computer, or cellular telephone.

Some of the advantages of embodiments of the present invention may be depending on the application: 1) power requirements for 2D transducers can be lowered, 2) fewer elements are required for similar beam pattern response 3) lower cost requirements for the transducer, 4) reduced requirements for electronic focusing 5) spot shaping when steering creates a more uniform near-field beam formation across steering angles required for ultrasound imaging (0 to 45 degrees, for example) and, 6) for the same number of elements, larger apertures may be used to provide a larger aperture which results in finer focusing characteristics.

Modifications to embodiments of the invention described in the foregoing are susceptible to being implemented without departing from the scope of the invention as defined by the appended claims.

The invention claimed is:

1. An ultrasound device having an array of elements, the array comprising:
   a first area including a first plurality of elements of a first type having a first functionality;
   a second area including a second plurality of elements of a second type having a second functionality; and
   a third area including a third plurality of elements of a third type having a third functionality different from the first functionality,
   wherein the second area further includes therein a fourth area including a number of elements that are switchable between the second and third types of functionality.

2. The ultrasound device according to claim 1, wherein the array includes a dynamic spot comprising:
   the fourth area including the number of elements that are switchable between the second and third types of functionality; and
   the third area including the third plurality of elements of the third type having the third functionality different from the first functionality.

3. The ultrasound device according to claim 2, wherein a size or shape of the dynamic spot during a receive mode of a beam is different from a size or shape of the dynamic spot during a transmit mode of the beam.

4. The ultrasound device according to claim 3, wherein the size or shape of the dynamic spot during the receive mode is different from the size or shape of the dynamic spot during the transmit mode based on switching performed by the number of elements in the fourth area.

5. The ultrasound device according to claim 3, wherein the size or shape of the dynamic spot during the receive mode of the beam is dynamic.

6. The ultrasound device according to claim 5, wherein the size or shape of the dynamic spot during a receive mode or transmit mode of a first beam is different from the size or shape of the dynamic spot during a receive mode or transmit mode of a second beam.

7. The ultrasound device according to claim 2, wherein the second plurality of elements are transmit/receive elements and the second functionality is a transmit functionality during a transmit mode and a receive functionality during a receive mode.

8. The ultrasound device according to claim 7, wherein the first plurality of elements are receive-only elements and the first functionality is a receive functionality.

9. The ultrasound device according to claim 7, wherein the first plurality of elements are transmit/receive elements and the first functionality is the transmit functionality during the transmit mode and the receive functionality during the receive mode.

10. The ultrasound device according to claim 7, wherein the first plurality of elements are transmit-only elements and the first functionality is a transmit functionality.

11. The ultrasound device according to claim 8, wherein the third plurality of elements are disabled elements and the third functionality is disabled.

12. The ultrasound device according to claim 10, wherein the third plurality of elements are disabled elements and the third functionality is disabled.

13. The ultrasound device according to claim 9, wherein the third plurality of elements are disabled elements and the third functionality is disabled.

14. The ultrasound device according to claim 7, wherein the dynamic spot has an elliptical, circular, or polygonal shape.

15. The ultrasound device according to claim 1, wherein the array has an elliptical shape or a polygonal shape.

16. An ultrasound device, comprising:
   a main processing unit;
   a probe part connected to the main processing unit;
   the array according to claim 1 integral to a handle part of the probe part; and
   an apodization unit configured to receive an ultrasound signal from the array, the signal having multiple channels, to determine a weight for each channel based on an apodization profile, wherein the apodization profile is one of ring-centered and edge-centered, and to multiply the received ultrasound signal by the determined weight for each channel.

17. An ultrasound device having an array of elements, the array comprising:
   a first area including a first plurality of elements of a first type having a first functionality and which do not transmit ultrasound signals;
   a second area including a second plurality of elements of a second type having a second functionality; and
   a third area including a third plurality of elements of a third type having a third functionality,
   wherein the array has an oblong ellipse shape, and
   wherein the first area is positioned inside the second area and the third area and the first area includes the center of the array.

18. The ultrasound device according to claim 17, wherein the second plurality of elements are transmit/receive elements and the second functionality is a transmit functionality during a transmit mode and a receive functionality during a receive mode.

19. The ultrasound device according to claim 18, wherein the first plurality of elements are receive-only elements and the first functionality is a receive functionality.

20. The ultrasound device according to claim 19, wherein the third plurality of elements are transmit-only elements and the third functionality is a transmit functionality.

21. The ultrasound device according to claim 19, wherein the third plurality of elements are receive-only elements and the third functionality is a receive functionality.

22. The ultrasound device according to claim 19, wherein the third plurality of elements are transmit/receive elements and the third functionality is the transmit functionality during the transmit mode and the receive functionality during the receive mode.

23. The ultrasound device according to claim 19, wherein the third plurality of elements are disabled elements and the third functionality is disabled.

24. The ultrasound device according to claim 17, wherein the third plurality of elements are transmit-only elements and the third functionality is a transmit functionality.

25. The ultrasound device according to claim 17, wherein the third plurality of elements are receive-only elements and the third functionality is a receive functionality.

26. The ultrasound device according to claim 17, wherein the third plurality of elements are transmit/receive elements and the third functionality is the transmit functionality during the transmit mode and the receive functionality during the receive mode.

27. The ultrasound device according to claim 17, wherein the third plurality of elements are disabled elements and the third functionality is disabled.

28. The ultrasound device according to claim 17, wherein the third plurality of elements are transmit-only elements and the third functionality is a transmit functionality.

29. The ultrasound device according to claim 17, wherein the third plurality of elements are receive-only elements and the third functionality is a receive functionality.

30. The ultrasound device according to claim 17, wherein the third plurality of elements are transmit/receive elements and the third functionality is the transmit functionality during the transmit mode and the receive functionality during the receive mode.

31. The ultrasound device according to claim 17, wherein the third plurality of elements are disabled elements and the third functionality is disabled.

32. A method of processing an ultrasound signal, the method comprising:

receiving the ultrasound signal from an array, the signal having multiple channels, wherein the array includes a first area including a first plurality of elements of a first type having a first functionality, a second area including a second plurality of elements of a second type having a second functionality, and a third area including a third plurality of elements of a third type having a third functionality different from the first functionality, wherein the second area further includes fourth area having a number of elements that are switchable between the second and third types of functionality;

determining a weight for each channel based on an apodization profile, wherein the apodization profile is one of ring-centered and edge-centered;

multiplying the received ultrasound signal by the determined weight for each channel; and displaying the multiplied ultrasound signal as an ultrasound image.

33. The method according to claim 32, further comprising:

summing a sub-array of elements of the array and applying the summation to each of the channels before the step of determining.

* * * * *